United States Patent
Zhang et al.

(10) Patent No.: US 12,319,931 B2
(45) Date of Patent: Jun. 3, 2025

(54) ONCOLYTIC VIRUS EXPRESSING INTERFERON AND APPLICATION THEREFOR

(71) Applicant: SHANGHAI YUANSONG BIOTECHNOLOGY CO. LTD., Shanghai (CN)

(72) Inventors: Kangjian Zhang, Shanghai (CN); Xianlong Fang, Shanghai (CN); Jinfa Gu, Shanghai (CN); Xinyuan Liu, Shanghai (CN)

(73) Assignee: SHANGHAI YUANSONG BIOTECHNOLOGY CO. LTD., Shanghai (CN)

( * ) Notice: Subject to any disclaimer, the term of this patent is extended or adjusted under 35 U.S.C. 154(b) by 931 days.

(21) Appl. No.: 17/418,759

(22) PCT Filed: Dec. 24, 2019

(86) PCT No.: PCT/CN2019/127782
§ 371 (c)(1),
(2) Date: Jun. 25, 2021

(87) PCT Pub. No.: WO2020/135390
PCT Pub. Date: Jul. 2, 2020

(65) Prior Publication Data
US 2022/0064670 A1 Mar. 3, 2022

(30) Foreign Application Priority Data
Dec. 26, 2018 (CN) .......................... 201811603052.2

(51) Int. Cl.
| | | |
|---|---|---|
| *C12N 15/86* | (2006.01) | |
| *A61P 35/00* | (2006.01) | |
| *A61P 35/04* | (2006.01) | |
| *C07K 14/555* | (2006.01) | |
| *C12N 7/00* | (2006.01) | |
| *A61K 38/00* | (2006.01) | |

(52) U.S. Cl.
CPC .............. *C12N 15/86* (2013.01); *A61P 35/00* (2018.01); *A61P 35/04* (2018.01); *C07K 14/555* (2013.01); *C12N 7/00* (2013.01); *A61K 38/00* (2013.01); *C12N 2710/10344* (2013.01); *C12N 2710/10345* (2013.01); *C12N 2710/16145* (2013.01); *C12N 2800/107* (2013.01)

(58) Field of Classification Search
CPC .... C12N 2800/107; C12N 15/86; C12N 7/00; C12N 2710/10344; C12N 2710/10345; C12N 2710/16145; A61P 35/04; A61P 35/00; C07K 14/555; A61K 38/00
See application file for complete search history.

(56) References Cited

U.S. PATENT DOCUMENTS

| | | | |
|---|---|---|---|
| 4,695,623 | A | 9/1987 | Stabinsky |
| 4,897,471 | A * | 1/1990 | Stabinsky .............. C12N 15/10 435/69.51 |
| 2004/0241142 | A1 | 12/2004 | Johnson et al. |
| 2005/0287119 | A1* | 12/2005 | Benedict ................ A61K 48/00 514/44 R |
| 2013/0065952 | A1 | 3/2013 | Koh et al. |
| 2014/0023619 | A1 | 1/2014 | Kosai et al. |
| 2016/0317591 | A1 | 11/2016 | Aboody et al. |
| 2017/0202893 | A1 | 7/2017 | O'Shea et al. |

FOREIGN PATENT DOCUMENTS

| | | |
|---|---|---|
| CN | 1509764 A | 7/2004 |
| CN | 1893981 A | 1/2007 |
| CN | 105769819 A | 7/2016 |
| CN | 106755103 A | 5/2017 |
| EP | 2537527 A2 | 12/2012 |
| JP | 2007503812 A | 3/2007 |
| JP | 2007513963 A | 5/2007 |
| JP | 2008532995 A | 8/2008 |
| KR | 10-2007-0111542 A | 11/2007 |
| WO | 2005021777 A2 | 3/2005 |
| WO | 2005/058368 A1 | 6/2005 |
| WO | 2005/115476 A1 | 12/2005 |
| WO | 2006134497 A2 | 12/2006 |
| WO | 2011/118819 A1 | 9/2011 |
| WO | 2018/078220 A1 | 5/2018 |
| WO | 2018/137643 A1 | 8/2018 |

OTHER PUBLICATIONS

Fukuhara, Hiroshi, Yasushi Ino, and Tomoki Todo. "Oncolytic virus therapy: A new era of cancer treatment at dawn." Cancer science 107.10 (2016): 1373-1379. (Year: 2016).*
Fuke, Motohiro, L. Cheryl Hendrix, and Arthur P. Bollon. "Pseudogene IFN-αL: removal of the stop codon in the signal sequence permits expression of active human interferon." Gene 32.1-2 (1984): 135-140. (Year: 1984).*
First Office Action dated Mar. 24, 2023 for Chinese patent application No. 201811603052.2, English translation provided by Google Translate.
First Office Action dated Mar. 30, 2023 for Chinese patent application No. 201980007573.8, English translation provided by Google Translate.
Hongling Huang, "1. Interferon-β-armed oncolytic adenovirus induces both apoptosis and Necroptosis in cancer cells; 2. Identification of novel components and function of Hippo signaling transduction pathway in *Drosophila melanogaster*", Docin.com , Jun. 13, 2014.
Second Office Action dated May 23, 2023 for Japanese patent application No. 2021-538122, English translation provided by Global Dossier.

(Continued)

*Primary Examiner* — Robert J Yamasaki
*Assistant Examiner* — Trevor Kane
(74) *Attorney, Agent, or Firm* — Yue (Robert) Xu; Apex Attorneys at Law, LLP

(57) ABSTRACT

Provided is an oncolytic virus expressing interferon. Specifically provided is an oncolytic adenovirus comprising a fusion protein expressing interferon, said oncolytic virus being capable of effectively suppressing tumors in vitro and in vivo.

16 Claims, 15 Drawing Sheets
Specification includes a Sequence Listing.

(56) References Cited

OTHER PUBLICATIONS

International Search Report for PCT/CN2019/127782 mailed Mar. 23, 2020, ISA/CN.

Peng Lin-hui, et al. The payload of mouse interferon-γ gene enhances the antitumor activity of the oncolytic adenovirus CNHK300 in hepatocellular carcinoma, Chinese Journal of Experimental Surgery, vol. 28, No. 6, Jun. 30, 2011, pp. 920-922.

Peng Lin-hui, et al. Killing effect and mIFN-γ expression of the replicative oncolytic adenovirus CNHK300-mIFN-γ on gastrointestinal malignant tumor in vitro, Chongqing Medical Journal, vol. 41, No. 22, Aug. 31, 2012, pp. 2233-2236.

Peng Lin-hui, et al. Killing effect and mIFN-γ expression of gene-viral therapeutic system CNHK300-mIFN-γ on malignant tumor cells in vitro, Chinese Journal of Pathophysiology, vol. 28, No. 5, Dec. 31, 2012, pp. 802-806.

First Office Action dated Jun. 20, 2022 for Chinese patent application No. 201980007573.8, English translation provided by Global Dossier.

Search Report dated Sep. 16, 2022 for European patent application No. 19902481.1.

First Office Action dated Aug. 16, 2022 for Japanese patent application No. 2021-538122, English translation provided by Global Dossier.

Kawamura Kiyoko, "Anti-tumor effects for solid tumors in digestive tracts were produced by a chimeric type of oncolytic adenoviruses and the carrier cells", Report on the research results of the Scientific Research Funded Project (Scientific research Grant), May 23, 2012, pp. 1-5.

First Office Action dated Jul. 31, 2023 for Korean patent application No. 10-2021-7023174, English translation provided by Global Dossier.

Christopher J. LaRocca, "Oncolytic adenovirus expressing interferon alpha in a syngeneic Syrian hamster model for the treatment of pancreatic cancer", Surgery, 2015, vol. 157, No. 5, pp. 888-898.

Ling Feng He, "Significant antitumor activity of oncolytic adenovirus expressing human interferon-β for hepatocellular carcinoma", J Gene Med 2008; 10: 983-992.

First Examination Report dated Oct. 28, 2022 for Australian Patent Application No. 2019412342.

Su CQ, et al., "Potent antitumoral efficacy of a novel replicative adenovirus CNHK300 targeting telomerase-positive cancer cells", J Cancer Res Clin Oncol. Oct. 2004;130(10):591-603. doi: 10.1007/s00432-004-0577-4.

\* cited by examiner

D

E

D

A

B

A

B

C

ONCOLYTIC VIRUS EXPRESSING INTERFERON AND APPLICATION THEREFOR

CROSS REFERENCE TO RELATED APPLICATIONS

This application is a US National Phase application based upon PCT Application No. PCT/CN2019/127782 filed Dec. 24, 2019, which claims the priority of Chinese Patent Application No. 201811603052.2, filed to China National Intellectual Property Administration on Dec. 26, 2018, and titled with "ONCOLYTIC VIRUS EXPRESSING INTERFERON AND APPLICATION THEREFOR", and the disclosures of which are hereby incorporated by reference in its entirety.

SEQUENCE LISTING

Sequence Listing is being submitted as an ASCII text file via EFS-Web, file name "210054-APXU-YSBIO-Sequence-listing.txt", size 8 KB, created on Jun. 24, 2021, the content of which is incorporated herein by reference.

FIELD

The present disclosure relates to the technical field of tumor therapy using an oncolytic virus, specifically to an oncolytic adenovirus expressing interferon, and preparation method and application thereof.

BACKGROUND

According to statistical reports, more than 12 million people worldwide are diagnosed with cancer per year, and cancer has a serious impact on the health and development of human beings. Affected by medical and environmental conditions, the cancer mortality rate in China is higher than the global average. Traditional tumor therapy has disadvantages such as poor efficacy, high mortality, and high prognostic recurrence rate, so it poses a major challenge to the treatment of cancer. For example, in the very early stage of tumor development, micrometastasis has already occurred and is located in tissues far away from the original site of the tumor. Therefore, when diagnosed with cancer, many patients have already experienced micrometastasis.

As an emerging therapy with broad prospects, the oncolytic virus can replicate within tumor cells and break the cells, thereby continuously killing tumor cells. Moreover, the oncolytic virus can also carry therapeutic gene and the like to exert the functions of antioncogenes to kill tumor cells while using the virus to lyse cells, thereby improving the therapeutic effect.

There is still an urgent need to enhance the efficacy of oncolytic viruses, thereby increasing the chance of clinical success.

SUMMARY

In the present disclosure, the structure of an oncolytic adenovirus genome is modified by replacing the wild-type promoter of E1A gene in viral genome with a survivin promoter, and then 24 base pairs (364-387 bp) of E1A gene responsible for encoding amino acids 122-129 of E1A protein are deleted, which prevents E1A protein from binding to Rb protein, and thus prevents the release of E2F which promotes the host cell to enter cell cycle. The modified oncolytic adenovirus can only selectively replicate in tumor cells with dysfunctional Rb protein.

Further, a nucleic acid sequence encoding interferon (such as consensus interferon) is introduced into the viral genome, especially the nucleic acid sequence shown in SEQ ID NO: 2, 3 or 4. As a result, it is found that the obtained oncolytic adenovirus has excellent tumor-suppressive effects in vitro and in vivo. It is particularly surprising that the oncolytic adenovirus of the present disclosure can effectively inhibit tumor growth at a location far away from the injection site and also effectively prevent tumor recurrence, which has immeasurable value for clinical application. Based on the above findings, the present disclosure has been completed.

The first aspect of the present disclosure provides an oncolytic virus comprising a nucleic acid encoding interferon.

In one embodiment, the virus is an adenovirus.

In another embodiment, the virus comprises E1A gene driven by a survivin promoter, preferably the endogenous promoter of the E1A gene in viral genome is replaced by the survivin promoter; and/or the E1A gene is modified so that the binding activity of E1A protein to Rb protein is reduced or completely inactivated. Preferably, the E1A gene is modified by deleting a sequence encoding amino acids 122-129 of the E1A protein, for example, by deleting nucleotides 364-387 in SEQ ID NO: 1.

(SEQ ID NO: 1)
ATGAGACATATTATCTGCCACGGAGGTGTTATTACCGAAGAAATGGCCG

CCAGTCTTTTGGACCAGCTGATCGAAGAGGTACTGGCTGATAATCTTCC

ACCTCCTAGCCATTTTGAACCACCTACCCTTCACGAACTGTATGATTTA

GACGTGACGGCCCCCGAAGATCCCAACGAGGAGGCGGTTTCGCAGATTT

TTCCCGACTCTGTAATGTTGGCGGTGCAGGAAGGGATTGACTTACTCAC

TTTTCCGCCGGCGCCCGGTTCTCCGGAGCCGCCTCACCTTTCCCGGCAG

CCCGAGCAGCCGGAGCAGAGAGCCTTGGGTCCGGTTTCTATGCCAAACC

TTGTACCGGAGGTGATCGATCTTACCTGCCACGAGGCTGGCTTTCCACC

CAGTGACGACGAGGATGAAGAGGGTGAGGAGTTTGTGTTAGATTATGTG

GAGCACCCCGGGCACGGTTGCAGGTCTTGTCATTATCACCGGAGGAATA

CGGGGGACCCAGATATTATGTGTTCGCTTTGCTATATGAGGACCTGTGG

CATGTTTGTCTACAGTAAGTGAAAATTATGGGCAGTGGGTGATAGAGTG

GTGGGTTTGGTGTGGTAATTTTTTTTTAATTTTTACAGTTTTGTGGTT

TAAAGAATTTTGTATTGTGATTTTTTTAAAAGGTCCTGTGTCTGAACCT

GAGCCTGAGCCCGAGCCAGAACCGGAGCCTGCAAGACCTACCCGCCGTC

CTAAAATGGCGCCTGCTATCCTGAGACGCCCGACATCACCTGTGTCTAG

AGAATGCAATAGTAGTACGGATAGCTGTGACTCCGGTCCTTCTAACACA

CCTCCTGAGATACACCCGGTGGTCCCGCTGTGCCCCATTAAACCAGTTG

CCGTGAGAGTTGGTGGGCGTCGCCAGGCTGTGGAATGTATCGAGGACTT

GCTTAACGAGCCTGGGCAACCTTTGGACTTGAGCTGTAAACGCCCCAGG

CCATAA.

In another embodiment, the interferon is interferon-α, interferon-β, interferon-γ or consensus interferon (such as Infergen). Preferably, the nucleic acid sequence encoding the interferon is shown in SEQ ID NO: 2, 3 or 4.

In another embodiment, the nucleic acid sequence is operably linked to a promoter. Preferably, the promoter is CMV promoter.

In another embodiment, the oncolytic virus is an oncolytic virus with an accession number of CCTCC NO: V201957. The deposit information is as follows: Depositary Authority: China Center for Type Culture Collection. Address: Wuhan, China. Deposit date: Aug. 27, 2019. Name/Reference: Recombinant Human Type 5 Adenovirus rAd-IFN-1-SP-E1A(Δ24 bp)-E1B. Accession number: CCTCC NO: V201957.

Or, the oncolytic virus is an oncolytic virus with an accession number of CCTCC NO: V201958. The deposit information is as follows: Depositary Authority: China Center for Type Culture Collection. Address: Wuhan, China. Deposit date: Aug. 27, 2019. Name/Reference: Recombinant Human Type 5 Adenovirus rAd-IFN-2-SP-E1A(Δ24 bp)-E1B. Accession number: CCTCC NO: V201958.

Or, the oncolytic virus is an oncolytic virus with an accession number of CCTCC NO: V201871, and its deposit information is as follows: Depositary Authority: China Center for Type Culture Collection. Address: Wuhan, China. Deposit date: Dec. 12, 2018. Name/Reference: Recombinant Human Type 5 Adenovirus rAd-IFN-3-SP-E1A(Δ24 bp)-E1B. Accession number: CCTCC NO: V201871.

The second aspect of the present disclosure provides use of the oncolytic virus of the first aspect in the manufacture of a medicament for the treatment of a proliferative disease. Preferably, the proliferative disease is a cancer, such as prostate cancer, breast cancer, colorectal cancer, lung cancer, liver cancer, melanoma, lymphoma, gastric cancer, esophageal cancer, ovarian cancer, head and neck squamous cell carcinoma, bladder cancer, glioma, cervical cancer, or kidney cancer.

The third aspect of the present disclosure provides a pharmaceutical composition comprising a pharmaceutically effective amount of the oncolytic virus of the first aspect, and optionally a pharmaceutically acceptable carrier.

In one embodiment, the pharmaceutical composition is formulated for intravenous, nebulized inhalation, perfusion, or intratumoral administration.

In another embodiment, the pharmaceutical composition comprises the oncolytic virus in an amount of about $10^8$ vp to $10^{12}$ vp (e.g., $1.5 \times 10^{10}$ vp).

The fourth aspect of the present disclosure provides a method for treating a proliferative disease, comprising administering the oncolytic virus of the first aspect or the pharmaceutical composition of the third aspect to a subject in need thereof, wherein the subject is, for example, a mammal, preferably human; and preferably, the proliferative disease is a cancer, such as prostate cancer, breast cancer, colorectal cancer, lung cancer, liver cancer, melanoma, lymphoma, gastric cancer, esophageal cancer, ovarian cancer, head and neck squamous cell carcinoma, bladder cancer, glioma, cervical cancer, or kidney cancer.

The fifth aspect of the present disclosure provides a method for preventing or inhibiting metastasis of cancer cells, comprising administering the oncolytic virus of the first aspect or the pharmaceutical composition of the third aspect to a subject in need thereof, wherein the subject is, for example, a mammal, preferably human; and the cancer is, for example, prostate cancer, breast cancer, colorectal cancer, lung cancer, liver cancer, melanoma, lymphoma, gastric cancer, esophageal cancer, ovarian cancer, head and neck squamous cell carcinoma, bladder cancer, glioma, cervical cancer, or kidney cancer.

The sixth aspect of the present disclosure provides a method for preventing cancer recurrence, comprising administering the oncolytic virus of the first aspect or the pharmaceutical composition of the third aspect to a subject in need thereof, wherein the subject is, for example, a mammal, preferably human; and the cancer is, for example, prostate cancer, breast cancer, colorectal cancer, lung cancer, liver cancer, melanoma, lymphoma, gastric cancer, esophageal cancer, ovarian cancer, head and neck squamous cell carcinoma, bladder cancer, glioma, cervical cancer, or kidney cancer.

In some specific embodiments of the above fourth to sixth aspects, the oncolytic virus is administered to the subject in an amount of about $10^8$ vp to $10^{12}$ vp (e.g., $1.5 \times 10^{10}$ vp) by intravenous, nebulized inhalation, perfusion, or intratumoral administration, with an administration number per treatment of 1-6 (for example, 1, 2, 3, 4, 5, or 6), an administration interval of every 1, 2, 3, 4, 5, 6, 7 or more days, or 1, 2, 3, 4, 5, 6 or more times over the course of one day, and a treatment number of 1-12 (for example, 1, 2, 3, 4, 5, 6, 7, 8, 9, 10, 11, or 12).

The recombinant oncolytic viruses provided by the present disclosure have good safety and excellent tumor-suppressive effect, which is significantly superior to the existing drugs sorafenib and gemcitabine. Compared with administering interferon protein or an oncolytic virus empty vector alone, the recombinant oncolytic viruses provided by the present disclosure achieve an unexpected synergistic effect. In addition, the oncolytic viruses of the present disclosure also exhibit the ability to inhibit tumor metastasis and recurrence, showing broad clinical application prospects.

BRIEF DESCRIPTION OF DRAWINGS

FIG. 3 shows that the oncolytic adenoviruses of the present disclosure increase the expression of MHC I, wherein FIG. 3A shows the result in SW780 cells and FIG. 3B shows the result in MCF-7 cells.

FIG. 5 shows the comparison of the inhibitory effects of recombinant oncolytic adenoviruses with different structures on tumor cells, wherein FIGS. 5A and 5B show the comparison of the inhibitory effects of replicative and non-replicative adenoviruses on liver cancer cell line Huh-7 and colon cancer cell line SW620, respectively, FIGS. 5C and 5D show the comparison of the inhibitory effects of the oncolytic virus carrying or not carrying interferon sequence on breast cancer cell line MDA-MB-231 and lung cancer cell line HCC827, respectively, and FIG. 5E shows the killing effect of the recombinant oncolytic adenovirus on normal liver fibroblast cell line HLF.

FIG. 6 shows the inhibitory effect of recombinant oncolytic adenovirus rAd-IFN-3-SP-E1A(Δ24 bp)-E1B on tumor growth in a xenograft model of nude mouse, wherein FIG. 6A shows the results of SW620 xenograft tumor model in nude mouse, FIGS. 6B and C show the results of MDA-MB-231 xenograft tumor model in nude mouse, and FIGS. 6D and 6E show the results of HCC827 xenograft tumor model in nude mouse.

FIG. 7 shows the comparison of the effects of the recombinant oncolytic adenovirus of the present disclosure, blank control, rIFN protein alone, no-load virus alone, and a combination of rIFN protein and no-load virus in breast cancer cell line HCC1806 xenograft tumor model in nude mouse, wherein FIG. 7A shows dosage regimen, and FIG. 7B shows the volume of xenograft tumors in each experimental group and control group.

FIG. 8 shows the in vivo drug efficacy of each recombinant oncolytic adenovirus of the present disclosure, wherein FIG. 8A shows the changes of tumor volume at the injection site, and FIG. 8B shows the changes of tumor volume at the non-injection site.

FIG. 9 shows the effect of recombinant oncolytic adenovirus rAd-IFN-3-SP-E1A(Δ24 bp)-E1B in preventing tumor recurrence, wherein FIG. 9A shows the effect of re-transplantation of HCC827 cells in HCC827 xenograft tumor model of nude mouse mice in which the xenograft tumors had been regressed by injection of rAd-IFN-3-SP-E1A(Δ24 bp)-E1B before, PBS group as control; FIG. 9B shows the tumor change data of each mouse in the experimental group, and FIG. 5C shows a statistical comparison of the final tumor volume of mice in the experimental group and the control group.

FIG. 10 shows the inhibitory effect of recombinant oncolytic adenovirus rAd-IFN-3-SP-E1A(Δ24 bp)-E1B on tumor growth in a xenograft tumor model of mouse with humanized immune system, wherein FIGS. 10A and 10B show the inhibitory effect on the tumor at the injection site (right side), and FIGS. 10C and 10D show the inhibitory effect on the tumor at the non-injection site (left side).

FIG. 11 shows the inhibitory effect of recombinant oncolytic adenovirus rAd-IFN-1-SP-E1A(Δ24 bp)-E1B on tumor growth in a PDX model of nude mouse, wherein FIG. 11A shows the inhibitory effect of the recombinant oncolytic adenovirus on lung squamous carcinoma PDX, FIG. 11B shows the inhibitory effect of the recombinant oncolytic adenovirus on lung adenocarcinoma PDX, and FIG. 11C shows the inhibitory effect of the recombinant oncolytic adenovirus on triple negative breast cancer PDX.

DETAILED DESCRIPTION

Figure 1:
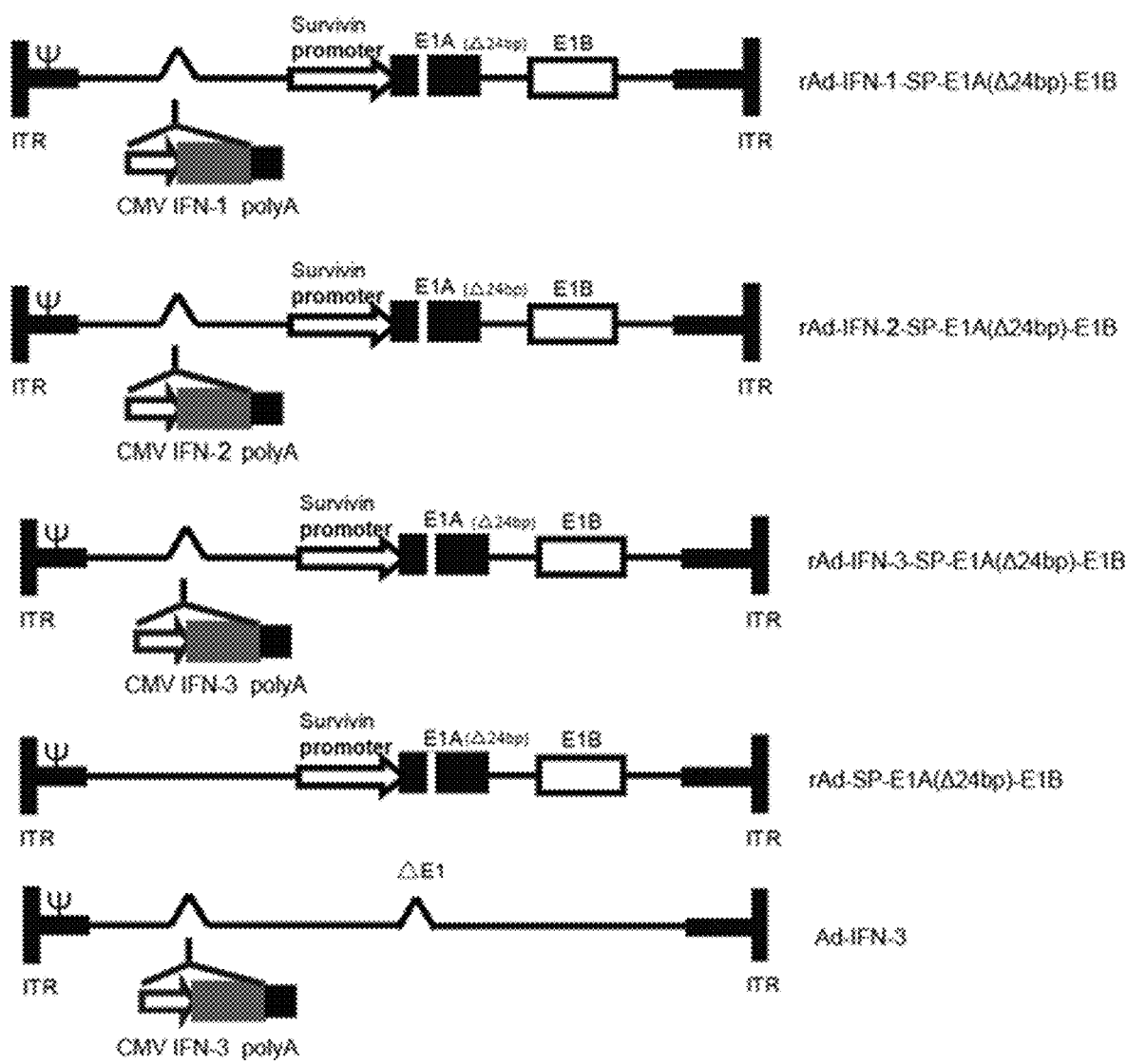
FIG. 1 shows schematic diagrams of various oncolytic adenovirus genomes.

The term used in this application has the same meaning as in the prior art. In order to clearly explain the meaning of the terms used, the specific meanings of some terms in this application are given below. When the definition herein conflicts with the conventional meaning of the term, the definition herein shall prevail.

Definitions

Unless otherwise defined, all technical and scientific terms used herein have the same meaning as commonly understood by those of ordinary skill in the art to which the present disclosure belongs. All publications mentioned herein are incorporated herein by reference for the purpose of describing and disclosing the cell lines, vectors, and methods reported in the publications, which can be used in the present disclosure. Nothing can be considered admitted herein, and the present disclosure does not have the right to precede such disclosures based on previous inventions.

The term "oncolytic virus" refers to a virus capable of selectively replicating in and slowing down the cell growth or inducing the death of a cancerous or hyperproliferative cell, while having no or minimal effect on normal cells. Exemplary oncolytic viruses include vesicular stomatitis virus (VSV), Newcastle disease virus (NDV), herpes simplex virus (HSV), reovirus, measles virus, retrovirus, influenza virus, Sinbis virus, vaccinia virus, and adenovirus (Reference could be made to Kirn et al., Nat. Med. 7:781 (2001); Coffey et al., Science 282: 1332 (1998); Lorence et al., Cancer Res. 54: 6017 (1994); and Peng et al., Blood 98: 2002 (2001)).

The term "interferon" refers to a family of secreted proteins produced by a variety of eukaryotic cells after exposure to various environmental stimuli (including viral infection or exposure to mitogens). In addition to having antiviral properties, interferon has also been shown to affect a variety of cell functions. There are three main interferon, IFN-α, IFN-β and IFN-γ. Interferon was originally classified according to its cellular origin (leukocytes, fibroblasts or T cells). Leukocyte-derived interferon is currently called IFN-α, fibroblast-derived interferon is IFN-β, and T cell-derived interferon is IFN-γ.

The term "consensus interferon" refers to a synthetic interferon whose amino acid sequence is roughly the average sequence of all known human interferon-a subtype sequences. It has been reported that consensus interferon has activities of antivirus, anti-proliferation and NK cell activation, which are better than (about 5 times) any natural human IFN-α subtype. For an exemplary consensus interferon such as Infergen, reference could be made to the sequences disclosed in U.S. Pat. Nos. 4,695,623 and 4,897,471.

The present disclosure can use interferon sequences known in the prior art. In a preferred embodiment, the present disclosure uses consensus interferon.

The inventors of the present disclosure unexpectedly found that selection of a suitable nucleic acid coding sequence would affect the in vivo therapeutic effect of interferon protein. For the same interferon protein, such as consensus interferon, when carrying different interferon nucleic acid coding sequences, the oncolytic virus exhibits quite different oncolytic effect in vivo. The applicant also found that this difference in effect has nothing to do with biological codon preference, that is, this difference in effect is not caused by whether the codons that are most suitable for human expression are utilized. In one embodiment, when using codons suitable for prokaryotic expression (for example, the IFN-3 sequence shown in SEQ ID NO: 4), excellent and unexpected technical effects are also obtained.

The coding sequence of the consensus interferon used in the present disclosure is as follows:

IFN-1:

(SEQ ID NO: 2)
ATGGCCCTGTCCTTCAGCCTGCTGATGGCCGTGCTGGTGCTGAGCTACA
AGTCCATCTGCTCCCTGGGCATGTGTGATCTGCCTCAGACACACTCCCT
GGGCAATAGAAGGGCCCTGATCCTGCTGGCCCAGATGAGAAGGATCAGC
CCCTTCTCCTGCCTGAAGGATAGACACGATTTTGGCTTCCCTCAGGAGG
AGTTCGACGGCAATCAGTTTCAGAAGGCCCAGGCCATCTCCGTGCTGCA
CGAGATGATCCAGCAGACCTTTAACCTGTTCTCCACAAAGGACTCCAGC
GCCGCCTGGGACGAGTCCCTGCTGGAGAAGTTTTACACAGAGCTGTACC
AGCAGCTGAACGATCTGGAGGCCTGCGTGATCCAGGAGGTGGGCGTGGA
GGAGACCCCCCTGATGAATGTGGATTCCATCCTGGCCGTGAAGAAGTAC
TTTCAGAGAATCACCCTGTACCTGACCGAGAAGAAGTACAGCCCTTGTG
CCTGGGAGGTGGTGAGAGCCGAGATCATGAGATCCTTTTCCCTGAGCAC
AAACCTGCAGGAGAGGCTGAGAAGGAAGGAGTGA;

IFN-2:

(SEQ ID NO: 3)
ATGGCCCTGTCCTTCTCCCTGCTGATGGCCGTGCTGGTGCTGAGCTACA
AGTCCATCTGCTCCCTGGGCATGTGCGACCTGCCTCAGACACACTCCCT
GGGCAATAGGAGAGCCCTGATCCTGCTGGCCCAGATGAGGAGGATCTCC
CCTTTTAGCTGCCTGAAGGATAGACACGATTTCGGCTTCCCTCAGGAGG
AGTTCGATGGCAATCAGTTCCAGAAGGCCCAGGCCATCAGCGTGCTGCA

-continued

```
CGAGATGATCCAGCAGACCTTCAATCTGTTTAGCACCAAGGACTCCAGC
GCCGCCTGGGACGAGTCCCTGCTGGAGAAGTTCTACACCGAGCTGTACC
AGCAGCTGAACGACCTGGAGGCCTGCGTGATCCAGGAGGTGGGCGTGGA
GGAGACCCCTCTGATGAATGTGGATAGCATCCTGGCCGTGAAGAAGTAC
TTTCAGAGAATCACACTGTACCTGACAGAGAAGAAGTACAGCCCCTGCG
CCTGGGAGGTGGTGAGGGCTGAGATCATGAGGAGCTTTTCCCTGTCCAC
AAACCTGCAGGAGAGGCTGAGAAGGAAGGAGTGA;

IFN-3:
                                        (SEQ ID NO: 4)
ATGGCCCTGTCCTTTTCTTTACTGATGGCCGTGCTGGTGCTCAGCTACA
AATCCATCTGTTCTCTGGGCATGTGCGACCTGCCGCAGACCCACTCCCT
GGGTAACCGTCGTGCTCTGATCCTGCTGGCTCAGATGCGTCGTATCTCC
CCGTTCTCCTGCCTGAAAGACCGTCACGACTTCGGTTTCCCGCAGGAAG
AATTCGACGGTAACCAGTTCCAGAAAGCTCAGGCTATCTCCGTTCTGCA
CGAAATGATCCAGCAGACCTTCAACCTGTTCTCCACCAAAGACTCCTCC
GCTGCTTGGGACGAATCCCTGCTGGAAAAATTCTACACCGAACTGTACC
AGCAGCTGAACGACCTGGAAGCTTGCGTTATCCAGGAAGTTGGTGTTGA
AGAAACCCCGCTGATGAACGTTGACTCCATCCTGGCTGTTAAAAAATAC
TTCCAGCGTATCACCCTGTACCTGACCGAAAAAAAATACTCCCCGTGCG
CTTGGGAAGTTGTTCGTGCTGAAATCATGCGTTCCTTCTCCCTGTCCAC
CAACCTGCAGGAACGTCTGCGTCGTAAAGAATAA.
```

The term "pharmaceutical composition" as used herein means a combination of at least one drug and optionally a pharmaceutically acceptable carrier or excipient that are combined together to achieve a particular purpose. In certain embodiments, the pharmaceutical composition includes combinations that are separated in time and/or space as long as they can work together to achieve the purpose of the present disclosure. For example, the components of the pharmaceutical composition may be administered to the subject as a whole or separately. When the ingredients contained in the pharmaceutical composition are separately administered to a subject, the ingredients may be administered to the subject simultaneously or sequentially. Preferably, the pharmaceutically acceptable carrier is water, a buffered aqueous solution, an isotonic saline solution such as PBS (phosphate buffered saline), glucose, mannitol, dextrose, lactose, starch, magnesium stearate, cellulose, magnesium carbonate, 0.3% glycerol, hyaluronic acid, or polyalkylene glycols such as polypropylene glycol, triglycerides and the like. The type of the pharmaceutically acceptable carrier used depends in particular on whether the composition according to the present disclosure is formulated for oral, nasal, intratumoral, perfusion, intradermal, subcutaneous, intramuscular, or intravenous administration. The composition according to the present disclosure may contain a lubricant, a preservative, a stabilizer, a wetting agent, an emulsifier, salts that affect osmotic pressure, a buffer, coloring substances, flavoring substances and/or aromatic substances, etc., as an additive.

"Administration" or "administering" means to provide a substance, such as a pharmaceutical composition, to a subject in a pharmacologically acceptable manner.

The dosage of a pharmaceutical composition provided to a subject refers to a dose sufficient to show its benefit to the administered subject, and may also be referred to herein as a "pharmaceutical effective amount" or "effective amount". The actual amount administered, as well as the rate and time-course of administration, will depend on the condition and severity of the subject being treated. Prescription of treatment, e.g., decisions on dosage, etc., is ultimately within the responsibility of general practitioners and other medical doctors and relies on decisions of them, and typically takes account of the disease being treated, the condition of the individual patient, the site of delivery, the method of administration, and other factors known to physicians.

In one embodiment of the present disclosure, the pharmaceutical composition comprises the oncolytic virus in an amount of $10^8$ vp to $10^{12}$ vp, such as $1\times10^8$, $1.5\times10^8$, $2\times10^8$, $2.5\times10^8$, $3\times10^8$, $3.5\times10^8$, $4\times10^8$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, $1.5\times10^9$, $2\times10^9$, $2.5\times10^9$, $3\times10^9$, $3.5\times10^9$, $4\times10^9$, $4.5\times10^9$, $5\times10^9$, $5.5\times10^9$, $6\times10^9$, $6.5\times10^9$, $7\times10^9$, $7.5\times10^9$, $8\times10^9$, $8.5\times10^9$, $9\times10^9$, $9.5\times10^9$, $1\times10^{10}$, $1.5\times10^{10}$, $2\times10^{10}$, $2.5\times10^{10}$, $3\times10^{10}$ $3.5\times10^{10}$, $4\times10^{10}$, $4.5\times10^{10}$, $5\times10^{10}$, $5.5\times10^{10}$, $6\times10^{10}$, $6.5\times10^{10}$, $7\times10^{10}$, $7.5\times10^{10}$, $8\times10^{10}$, $8.5\times10^{10}$, $9\times10^{10}$, $9.5\times10^{10}$, $1\times10^{11}$, $1.5\times10^{11}$, $2\times10^{11}$, $2.5\times10^{11}$, $3\times10^{11}$, $3.5\times10^{11}$, $4\times10^{11}$, $4.5\times10^{11}$, $5\times10^{11}$, $5.5\times10^{11}$, $6\times10^{11}$, $6.5\times10^{11}$, $7\times10^{11}$, $7.5\times10^{11}$, $8\times10^{11}$, $8.5\times10^{11}$, $9\times10^{11}$, $9.5\times10^{11}$ or $1\times10^{12}$ vp, and any dosage between the above two.

In another embodiment, a single dose of the oncolytic virus administered to the subject is in an amount of $10^8$ vp to $10^{12}$ vp, such as $1\times10^8$, $1.5\times10^8$, $2\times10^8$, $2.5\times10^8$, $3\times10^8$, $3.5\times10^8$, $4\times10^8$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, $1.5\times10^9$, $2\times10^9$, $2.5\times10^9$, $3\times10^9$, $3.5\times10^9$, $4\times10^9$, $4.5\times10^9$, $5\times10^9$, $5.5\times10^9$, $6\times10^9$, $6.5\times10^9$, $7\times10^9$, $7.5\times10^9$, $8\times10^9$, $8.5\times10^9$, $9\times10^9$, $9.5\times10^9$, $1\times10^{10}$, $1.5\times10^{10}$, $2\times10^{10}$, $2.5\times10^{10}$, $3\times10^{10}$, $3.5\times10^{10}$, $4\times10^{10}$, $4.5\times10^{10}$, $5\times10^{10}$, $5.5\times10^{10}$, $6\times10^{10}$, $6.5\times10^{10}$, $7\times10^{10}$, $7.5\times10^{10}$, $8\times10^{10}$, $8.5\times10^{10}$, $9\times10^{10}$, $9.5\times10^{10}$, $1\times10^{11}$, $1.5\times10^{11}$, $2\times10^{11}$, $2.5\times10^{11}$, $3\times10^{11}$, $3.5\times10^{11}$, $4\times10^{11}$, $4.5\times10^{11}$, $5\times10^{11}$, $5.5\times10^{11}$, $6\times10^{11}$, $6.5\times10^{11}$, $7\times10^{11}$, $7.5\times10^{11}$, $8\times10^{11}$, $8.5\times10^{11}$, $9\times10^{11}$, $9.5\times10^{11}$ or $1\times10^{12}$ vp, and any dosage between the above two. The administration number per course of treatment is 1-6, for example, 1, 2, 3, 4, 5 or 6, and the administration interval can be 1-7 days, for example, 1, 2, 3, 4, 5, 6, 7 days.

In the present disclosure, the unit of virus dose is vp (viral particle), which represents the number of virus particles contained in the virus solution, and is virus particle titer.

The term "subject" as used herein means animals, including warm-blooded mammals such as human and primate; birds; domesticated domestic or farm animals such as cats, dogs, sheep, goats, cattle, horses and pigs; laboratory animals such as mice, rats and guinea pigs; fish; reptiles; zoo animals and wild animals, etc.

It should also be noted that if a specific numerical value is mentioned herein, at least that value will be included, unless the context clearly indicates that it refers otherwise. When a numerical value represents an approximate value, it should be understood that the specific numerical value forms another embodiment. As used herein, "about X" (where X is a number) means±10% (inclusive) of the listed value. If present, all ranges are inclusive and combinable.

Terms such as "comprising", "including", and "containing" as used herein are not intended to be limiting. In addition, unless otherwise indicated, "or" means "and/or".

Unless otherwise specified, any component, element, attribute or step disclosed in an embodiment of the method and product can be applied to any other method and product disclosed herein.

Each patent, patent application, cited publication, or description in this document of this disclosure is incorporated herein by reference in its entirety.

The present disclosure is further defined in the following examples. It should be understood that these examples are provided for illustration only and are not intended to limit the scope of the present disclosure. From the above discussion and these examples, those skilled in the art can determine the essential characteristics of the present disclosure, and make various changes and modifications to the present disclosure to adapt it to various usages and conditions without departing from the spirit and scope of the present disclosure.

Materials and Methods

I. Construction of recombinant oncolytic adenoviruses rAd-IFN-1-SP-E1A(Δ24 bp)-E1B, rAd-IFN-2-SP-E1A(Δ24 bp)-E1B and rAd-IFN-3-SP-E1A(Δ24 bp)-E1B The construction process of the above three viruses is similar, where the difference lies in the coding sequence of the consensus interferon used in the construction. The rAd-IFN-1-SP-E1A(Δ24 bp)-E1 construct used the coding sequence shown in SEQ IN NO: 2, the RAd-IFN-2-SP-E1A (Δ24 bp)-E1 construct used the coding sequence shown in SEQ ID NO: 3, and the rAd-IFN-3-SP-E1A(Δ24 bp)-E1 construct used the coding sequence shown in SEQ ID NO: 4. Taking the construction process of rAd-IFN-3-SP-E1A (Δ24 bp)-E1 as an example, a construction process of an recombinant oncolytic adenovirus is described in detail below, and the other two oncolytic adenovirus constructs can be constructed just by replacing the coding sequence of consensus interferon in rAd-IFN-3-SP-E1A(Δ24 bp)-E1 with the other two sequences.

i. Construction of Recombinant Plasmid pShuttle-IFN-3-SP-E1A(Δ24 bp)-E1B

A nucleotide sequence with NotI restriction site at 5' end and XbaI restriction site at 3' end (as shown in SEQ ID NO: 5) was synthesized by commissioning gene synthesis company, and the coding sequence of consensus interferon is shown in SEQ ID NO: 4.

(SEQ ID NO: 5)
ataagaatgcggccgcctcgactaattccctggcattatgcccagtaca tgacctatgggactttcctacttggcagtacatctacgtattagtcat cgctattaccatggtgatgcggttttggcagtacatcaatgggcgtgga tagcggtttgactcacggggatttccaagtctccaccccattgacgtca atgggagtttgttttggcaccaaaatcaacgggactttccaaaatgtcg taacaactccgccccattgacgcaaatgggcggtaggcgtgtacggtgg gaggtctatataagcagagctcgtttagtgaaccgtcagatcgcctgga gacgccatccacgctgttttgacctccatagaagacaccgggaccgatc cagcctggggatcttcgagtcgtcaagcttgaattcgatccccgggctg caggaattcccaatactatggccctgtccttttctttactgatggccgt gctggtgctcagctacaaatccatctgttctctgggcatgtgcgacctg ccgcagacccactccctgggtaaccgtcgtgctctgatcctgctggctc agatgcgtcgtatctccccgttctcctgcctgaaagaccgtcacgactt cggtttcccgcaggaagaattcgacggtaaccagttccagaaagctcag gctatctccgttctgcacgaaatgatccagcagaccttcaacctgttct ccaccaaagactcctccgctgcttgggacgaatccctgctggaaaaatt ctacaccgaactgtaccagcagctgaacgacctggaagcttgcgttatc caggaagttggtgttgaagaaaccccgctgatgaacgttgactccatcc tggctgttaaaaaatacttccagcgtatcaccctgtacctgaccgaaaaa aaaatactcccgtgcgcttgggaagttgttcgtgctgaaatcatgcgt tccttctccctgtccaccaacctgcaggaacgtctgcgtcgtaaagaat aaggatccatcgagcaacttgtttattgcagcttataatggttacaaat aaagcaatagcatcacaaatttcacaaataaagcattttttcactgca ttctagttgtggtttgtccaaactcatcaatgtatcttatcatgtctgg atcgtgtcgagcgcgttctttgaaagcagtcgaggggggcgctaggtgtg ggcagggacgagctggcgcggcgtcgctgggtgcaccgcgaccacgggc agagccacgcggcgggaggactacaactcccggcacaccccgcgccgcc ccgcctctactcccagaaggccgcgggggggaccgcctaagagggcgt gcgctcccgacatgccccgcggcgcgccattaaccgccagatttgaatc gccggaccccgttggcagaggtggcggcggcggcatacgtactgaaaatg agacatattatctgccacggaggtgttattaccgaagaaatggccgcca gtcttttggaccagctgatcgaagaggtactggctgataatcttccacc tcctagccattttgaaccacctacccttcacgaactgtatgatttagac gtgacggccccccgaagatcccaacgaggaggcggtttcgcagattttc ccgactctgtaatgttggcggtgcaggaagggattgacttactcactttt tccgccggcgcccggttctccggagccgcctcaccctttcccggcagccc gagcagccggagcagagagccttgggtccggtttctatgccaaaccttg taccggaggtgatcgatccacccagtgacgacgaggatgaagagggtga ggagtttgtgttagattatgtggagcaccccgggcacggttgcaggtct tgtcattatcaccggaggaatacggggacccagatattatgtgttcgc tttgctatatgaggacctgtggcatgtttgtctacagtaagtgaaaatt atgggcagtgggtgatagagtggtgggtttggtgtggtaatttttttt taatttttacagttttgtggtttaaagaattttgtattgtgatttttt aaaaggtcctgtgtctgaacctgagcctgagcccgagccagaaccggag cctgcaagacctacccgccgtcctaaaatggcgcctgctatcctgagac gcccgacatcacctgtgtctagagc.

The nucleic acid fragment shown in SEQ ID NO: 5 was subjected to double restriction digestion with NotI and XbaI, followed by recovering the digested fragment. The restriction digestion system is as follows:

| | |
|---|---|
| DNA fragment shown in SEQ ID NO: 5 | 10 μL |
| NotI | 0.5 μL |
| XbaI | 0.5 μL |
| 10× Buffer | 2 μL |
| ddH₂O | 7 μL |
| Total | 20 μL |

The above reaction system was placed in a 37° C. water bath for 2 hours.

Construction of pShuttle-E1A-E1B Plasmid

The pShuttle plasmid (Shanghai Jiran Biotechnology Co., Ltd.) and the adenovirus vector pXC2 plasmid (a gift from Academician Liu Xinyuan, Shanghai Institute of Biochemistry and Cell Biology, Shanghai Institutes for Biological Sciences, Chinese Academy of Sciences) were subjected to double restriction digestion with XhoI and MfeI, and the restriction digestion systems are as follows:

| Double restriction digestion system with XhoI and MfeI for pShuttle | |
|---|---|
| pShuttle | 10 μL |
| XhoI | 0.5 μL |
| MfeI | 0.5 μL |
| 10× Buffer | 2 μL |
| ddH₂O | 7 μL |
| Total | 20 μL |

| Double restriction digestion system with XhoI and MfeI for pXC2 | |
|---|---|
| pXC2 | 10 μL |
| XhoI | 0.5 μL |
| MfeI | 0.5 μL |
| 10× Buffer | 2 μL |
| ddH₂O | 7 μL |
| Total | 20 μL |

The above reaction system was placed in a 37° C. water bath for 2 h, and then subjected to agarose gel electrophoresis to recover the large fragment digested from pShuttle plasmid and the small fragment digested from pXC2 plasmid. Then the above recovered products were ligated using ligase to construct pShuttle-E1A-E1B plasmid, and the ligation system is as follows:

| | |
|---|---|
| Linearized pShuttle plasmid | 4 μL |
| Linearized pXC2 plasmid | 2 μL |
| Ligation High | 4 μL |
| Total | 10 μL |

The above reaction system was placed in a water bath at 16° C. for 2 hours, and the ligation product obtained was pShuttle-E1A-E1B.

The plasmid pShuttle-E1A-E1B was subjected to double restriction digestion with NotI and XbaI, followed by recovering the digested large fragment (vector fragment). Then the digested nucleic acid fragment and vector fragment were ligated using Ligation High ligase (TOYOBO™). The ligation system is as follows:

| | |
|---|---|
| Digested pShuttle-E1A-E1B plasmid fragment | 0.5 μL |
| Digested nucleic acid fragment | 5.5 μL |
| Ligation High | 4 μL |
| Total | 10 μL |

The above reaction system was placed in a water bath at 16° C. for 2 hours, and the ligation product obtained was pShuttle-IFN-3-SP-E1A(Δ24 bp)-E1B.

ii. Construction of Recombinant Plasmid pAd-IFN-3-SP-E1A(Δ24 bp)-E1B 1. pShuttle-IFN-3-SP-E1A(Δ24 bp)-E1B was subjected to single restriction digestion with PmeI enzyme for linearization, and the reaction system is as follows:

| | |
|---|---|
| pShuttle-IFN-3-SP-E1A(A24bp)-E1B | 8 μL |
| PmeI | 1 μL |
| 10× Buffer | 2 μL |
| ddH₂O | 9 μL |
| Total | 20 μL |

The above reaction system was placed in a 37° C. water bath for 1 hour, followed by dephosphorylation reaction.

2. FastAp was used to dephosphorylate the linearized pShuttle-IFN-3-SP-E1A(Δ24 bp)-E1B plasmid in step 1, and the reaction system is as follows:

| | |
|---|---|
| Linearized pShuttle-IFN-3-SP-E1A(A24bp)-E1B | 8 μL |
| FastAp | 1 μL |
| 10× Buffer | 2 μL |
| ddH₂O | 9 μL |
| Total | 20 L |

The above reaction system was placed in a 37° C. water bath for 1 hour, followed by transformation.

3. The adenovirus backbone plasmid was recombined with linearized pShuttle-IFN-3-SP-E1A(Δ24 bp)-E1B in BJ5183 competent cells to generate the recombinant plasmid pAd-IFN-3-SP-E1A(Δ24 bp)-E1B. The specific steps are as follows:

(1) The linearized pShuttle-IFN-3-SP-E1A(Δ24 bp)-E1B in the previous step was transformed into BJ5183 competent cells and then the cells were spread on the plate. Afterward, several single colonies were picked and cultured overnight with shaking.

(2) The plasmid was extracted from the cultured bacterial cells using a plasmid extraction kit.

The preparation method of BJ5183 competent cells can be found in Chinese patent application No. CN201810651914.2, which is briefly described as follows.

The plasmid pBHGE3 (purchased from Shanghai Gemple biotech Co., Ltd.) was subjected to restriction digestion with HindIII, while the plasmid pAdEasy-1 (purchased from Shanghai Jiran Biotechnology Co., Ltd.) was subjected to restriction digestion with SpeI, and the above two digested plasmids were then co-transformed into E. coli BJ5183 for homologous recombination to generate a recombinant adenovirus backbone plasmid carrying E3 region. Then, the recombinant adenovirus backbone plasmid was transformed into E. coli DH5α for amplification to generate the recombinant adenovirus backbone plasmid. Next, the recombinant adenovirus backbone plasmid was transformed into E. coli BJ5183 competent cells to generate the E. coli BJ5183 carrying the recombinant adenovirus backbone plasmid. Finally, the E. coli cells were prepared into a competent cell, which was used as the BJ5183 competence cells in step (1).

4. Restriction digestion identification.

The recombinant plasmid pAd-IFN-3-SP-E1A(Δ24 bp)-E1B was transformed into E. coli DH5α competent cells, and then the cells were spread on the plate. Afterward, several single colonies were picked and cultured with shaking. The plasmid was extracted from the cultured bacterial cells for restriction digestion identification. The restriction digestion system is as follows:

| | |
|---|---|
| pAd-IFN-3-SP-E1A(A24bp)-E1B | 8 pL |
| MluI | 1 μL |

| | |
|---|---|
| 10× Buffer | 2 μL |
| ddH₂O | 9 μL |
| Total | 20 μL |

The above reaction system was placed in a 37° C. water bath for 30 min, and then subjected to electrophoresis identification.

iii. Packaging of Recombinant Virus rAd-IFN-3-SP-E1A (Δ24 bp)-E1B

1. Cell culture

HEK-293 cells were cultured in a 6-well plate and allowed to reach 60%-80% confluence the next day.

2. The recombinant plasmid pAd-IFN-3-SP-E1A(Δ24 bp)-E1B was subjected to restriction digestion with PacI for linearization, and the reaction system is as follows:

| | |
|---|---|
| pAd-IFN-3-SP-E1A(A24bp)-E1B | 1 ug |
| PacI | 1 μL |
| 10× Buffer | 2 μL |
| ddH₂O | up to 20 μL |

3. Plasmid transfection and virus packaging

According to the instruction of Effectene™ Transfection Reagent kit, 1 g of the recombinant plasmid pAd-IFN-3-SP-E1A(Δ24 bp)-E1B linearized in step 2 was transfected into the HEK-293 cells seeded in the 6-well plate of step 1. After about 7-10 days, when the cells were completely broken, the supernatant containing viruses was collected and stored at −80° C. for later use.

iv. Titer Determination of Recombinant Virus

The principle of virus titer determination is to determine the number of viruses with infectious activity based on the number of hexon-stained positive cells by immunocytochemistry. According to the instructions of the adenovirus titer kit, the virus titer of the amplified and purified adenovirus was determined.

II. Detection of the Functions of Recombinant Oncolytic Adenovirus i. Western Blot Detection of Target Protein Expression 1. Cell Infection and Sample Harvest MDA-MB-231 cells were cultured in a 6-well plate with 5×105 cells per well in a CO2 incubator. In the next day, the MDA-MB-231 cells were infected with an no-load control virus rAd-SP-E1A(Δ24 bp)-E1B and recombinant oncolytic adenoviruses rAd-IFN-1-SP-E1A(Δ24 bp)-E1B, rAd-IFN-2-SP-E1A(Δ24 bp)-E1B, and rAd-IFN-3-SP-E1A(Δ24 bp)-E1B respectively at an inoculation ratio of 10 MOI. one well for each infection, followed by culturing in a CO2 incubator for 24 hours. The supernatant was discarded, and 100 μl RIPA Lysis Buffer™ per well was added to lyse cells. The lysate was collected as a test sample.

2. Pretreatment of Protein Sample

BCA protein quantification kit (purchased from Thermo™) was used to determine the protein concentration of each sample collected in step 1, and specific procedures can be found in the kit's instruction manual. Then RIPA Lysis Buffer™ was used to adjust the concentration of each sample according to the measurement to make the protein concentration in all samples consistent. Next, an appropriate volume of 5×SDS loading buffer (purchased from Beyotime) was added to each sample to make the final concentration as 1×. The samples were mixed well and placed in a metal bath at 100° C. for 10 min. The samples were directly used for Western analysis or stored in a refrigerator at −20° C.

3. Western Blot Analysis

SDS-PAGE gel electrophoresis was performed with a loading amount of 20 g of each pre-treated protein per slot. The proteins in the gel were transferred to PVDF membrane by using Biorad electrophoresis apparatus. The membrane was blocked with 5% non-fat milk for 30 min, and then incubated with rIFN antibody (HuaBio) and β-tubulin antibody (purchased from CoWin Biosciences) diluted to working concentration overnight at 4° C. with shaking. Afterward, the primary antibody was discarded and the membrane was washed 3 times with PBST buffer, and then the corresponding secondary antibody (purchased from Beyotime™) diluted to the working concentration was added. The membrane was subsequently incubated with the secondary antibody for 2 h at room temperature with shaking. Afterward, the secondary antibody was discarded and the membrane was washed 3 times with PBST buffer. ECL luminescent chromogenic kit (purchased from Yeasen™) was used to develop the color, and specific procedures can be found in the kit's instruction manual.

ii. Detection of MHC I Expression Regulated by Interferon.

1. Cell Culture and Virus Inoculation

SW780 cells and MCF-7 cells were cultured in 24-well plates at a density of $1.5×10^5$ cells per well, 500 l/well, in a $CO_2$ incubator. The next day, the cells were infected with no-load control virus rAd-SP-E1A(Δ24 bp)-E1B and recombinant oncolytic adenoviruses rAd-IFN-1-SP-E1A(Δ24 bp)-E1B, rAd-IFN-2-SP-E1A(Δ24 bp)-E1B, and rAd-IFN-3-SP-E1A(Δ24 bp)-E1B respectively at an inoculation ratio of 1 MOI, with an inoculation volume is 100 μl/well. In addition, a blank control group without virus (PBS group) was set up for each cell type. After treatment, the plates were shaken gently to mix well and cultured in a $CO_2$ incubator for 24 h.

2. Sample Treatment and Flow Cytometry Analysis

The supernatants of the cells after 24 hours treatment as described above were discarded. Then the cells were washed once with 1×PBS and 200 μl/well of digestion solution Accutase™ was added. After all the cells became round and detached after gently shaking, 800 μl of 1×PBS was added, and the cells were pipetted 5 times repeatedly. The cell mixture was transferred to a 1.5 ml EP tube followed by centrifugation at 1,500 rpm for 5 min. Afterward, the supernatant was discarded, and 1 ml of 1×PBS was added to wash and centrifuge again. Then, for each sample, 60 μl of antibody working solution (1 μl antibody stock solution in 240 μl 1×PBS) was added to the cells after washing and centrifugation. After mixing well, the cells were stained for 30 min in dark at room temperature. The unstained cells were as a negative control. After staining, the cells were washed with 1×PBS and centrifuged once. The cells were fixed with 2% PFA at room temperature for 10 min and flow cytometry analysis (according to the instructions of instrument) was performed with a loading volume of 50 μl/sample.

iii. Determination of Virus Replication Ratio

1. Cell Culture and Virus Inoculation

The breast cancer cell line MDA-MB-231 and normal breast cell line MCF-10A were cultured in a 6-well plate at a density of $1.2×10^6$ and $8×10^5$ cells/well respectively, 2 ml/well, in a $CO_2$ incubator until the next day. Then, the cells were infected with recombinant oncolytic adenoviruses rAd-IFN-1-SP-E1A(Δ24 bp)-E1B, rAd-IFN-2-SP-E1A(Δ24 bp)-E1B, and rAd-IFN-3-SP-E1A(Δ24 bp)-E1B respectively at an inoculation ratio of 1 MOI, with an inoculation volume of 100 μl/well, triplicates for each type of virus. After treatment, the plates were shaken gently to mix well and cultured in a $CO_2$ incubator for 72 h.

2. Sample Harvest, Pretreatment and Aliquoting

The 6-well plate cultured with the cells and treated for 72 hours was sealed with parafilm around, and stored in a −80° C. refrigerator. Three freeze-thaw cycles were carried out from −80° C. to room temperature. After the third thawing, the cells were pipetted off and mixed well with culture medium. Considering the liquid evaporation during the culture process, the total volume of the sample in each well needed to be made up to 2 ml with culture medium in the end. The samples were mixed well and divided into 3 aliquots (one for titer detection, and two for later use), and then stored at −80° C.

3. Titer Determination and Calculation of Virus Replication Ratio

One of the above aliquots was used for titer detection by QuickTiter™ Adenovirus Titer Immunoassay Kit from Cell Biolabs. The principle of this detection is to determine the number of viruses with infectious activity based on the number of hexon-stained positive cells by immunocytochemistry. The specific protocols are as follows:

(1) 293A cells were seeded in a 24-well plate (1 ml/well) at a density of $2.5\times10^5$ cells/well. After the cells were attached to the wall (approximately 24 h), 100 μl of virus to be tested after gradient dilution was added to each well. The well without virus was used as a blank control, and two duplicate wells were set for each gradient. Then the cells were cultured under a condition of 37° C. and 5% $CO_2$.

(2) After culture for 2 days, in a biological safety hood, the supernatant in the 24-well plate was discarded using a pipet, then 500 μl/well of methanol pre-cooled at −20° C. was added to each well. Afterward, the plate was placed in a refrigerator at −20° C. for 20 min.

(3) The cells were washed gently with 1×PBS 3 times, and blocked with 1% BSA for 1 h.

(4) 1% BSA was discarded, and the pre-diluted primary antibody anti-Hexon was added at 250 μl/well and incubated for 1 h at room temperature.

(5) The cells were washed gently with 1×PBS 3 times, and the pre-diluted secondary antibody (HRP) was added at 250 μl/well and incubated for 1 h at room temperature.

(6) The cells were washed gently with 1×PBS 3 times, and 1×DAB working solution was added to stain for 15 min at room temperature.

(7) The cells were washed gently with 1×PBS twice, and 1×PBS was added at 200 1/well to prevent the cells from drying out.

(8) A microscope setting to 10× objective lens and 10× eyepiece lens was used to take pictures. Nine fields were selected for each well (upper, lower, left, right, upper left, lower left, upper right, lower right, and center) for taking pictures.

(9) The number of virus units in each field of view under the corresponding dilution gradient was counted, and the gradient of about 50 virus units per field was regarded as the optimal counting gradient. If it is assumed that the average number of positive points in each field obtained by actual counting is Y, then the virus titer (IFU/ml) is: 135.2×Y× dilution factor.

The titer value of each sample multiplied by the total sample volume of 2 ml is the total yield of each sample well. Finally, the replication factor of each sample was calculated, and the virus replication ratio=total yield (total amount)/initial inoculation amount.

iv. Detection of the Safety of Oncolytic Virus by Crystal Violet Method

The cells were seeded in a 24-well plate. One day later, the cells were infected with the recombinant adenovirus to be tested at appropriate MOI. After 4 days of culture at 37° C., the culture medium was discarded, and 500 μL of crystal violet staining solution (2% crystal violet in 20% methanol solution) was added to each well to stain for 30 min, and then the excess staining solution was washed away with clean water. Pictures were taken after the plate became dry.

v. In Vivo Drug Efficacy Test

SW620 Xenograft Tumor Model in Nude Mice

When the experimental nude mice reached 6 weeks old, they were injected with $1\times10^6$ SW620 cells for tumor formation. When the tumor sizes were about 80-100 mm³ and the mice were in normal condition, the mice were randomly divided into three groups, namely PBS group, rAd-IFN-3-SP-E1A(Δ24 bp)-E1B group and Ad-IFN-3-SP-E1A(Δ24 bp)-E1B group. Mice in each group were all injected intratumorally with the desired virus at a dose of $1.5\times10^{10}$ vp/mouse/time, once every other day and a total of 4 times. The tumor size was observed and measured every 3 days.

MDA-MB-231 Xenograft Tumor Model in Nude Mice

When the experimental nude mice reached 5 weeks old, they were injected with $2\times10^6$ MDA-MB-231 cells for tumor formation. When the tumor sizes were about 80-100 mm³ and the mice were in normal condition, the mice were randomly divided into three groups, namely PBS group (intratumoral administration, once every other day, a total of 4 times), positive drug sorafenib group (gavage, single dose of 30 mg/kg, once every day for 14 days) and rAd-IFN-3-SP-E1A(Δ24 bp)-E1B group (intratumoral administration, a dose of $1.5\times10^{10}$ vp/mouse/time, once every other day, a total of 4 times), with each group of 8 mice. The tumor size was observed and measured every 3 days.

HCC827xenograft Tumor Model in Nude Mice

When the experimental nude mice reached 5 weeks old, they were injected with $2\times10^6$ HCC827 cells for tumor formation. When the tumor sizes were about 80-100 mm³ and the mice were in normal condition, the mice were randomly divided into four groups, namely PBS group (n=8, intratumoral administration, once every other day, a total of 4 times), positive drug sorafenib group (n=5, gavage, a dose of 30 mg/kg, once every day for 14 days), positive drug gemcitabine group (n=5, tail vein injection, a dose of 120 mg/kg, once every 4 days, a total of 4 times) and rAd-IFN-3-SP-E1A(Δ24 bp)-E1B group (n=5, intratumoral administration, a dose of $1.5\times10^{10}$ vp/mouse/time, once every other day, a total of 4 times). The tumor size was observed and measured every 3 days.

HCC1806xenograft Tumor Model in Nude Mice

When the experimental nude mice reached 5 weeks old, they were injected with $2\times10^6$ HCC1806 tumor cells for tumor formation. When the tumor sizes were about 80-100 mm3 and the mice were in normal condition, the mice were randomly divided into five groups, namely, virus preservation solution (vehicle) group (n=5, intratumoral administration, once every other day, a total of 5 times), recombinant interferon rIFN (20 μg/mouse/time) group (n=5, intraperitoneal injection, once every other day, a total of 5 times), no-load oncolytic virus rAd-SP-E1A(Δ24 bp)-E1B group (n=5, intratumoral administration, a dose of $1.5\times10^{10}$ vp/mouse/time, once every other day, a total of 5 times), a combination of no-load oncolytic virus and recombinant interferon rIFN+rAd-SP-E1A(Δ24 bp)-E1B group (n=5; for no-load oncolytic virus: intratumoral administration, a dose of 1.5×10$^{10}$ vp/mouse/time, once every other day, a total of 5 times; for rIFN: intraperitoneal injection, once every other day, a total of 5 times), and recombinant oncolytic virus rAd-IFN-1-SP-E1A(Δ24 bp)-E1B group (n=5, intratumoral administration, a dose of 1.5×10$^{10}$ vp/mouse/time, once every other day, a total of 5 times). The first administration of oncolytic virus was the day of grouping, and the first administration of recombinant interferon was the second day of grouping. The tumor size was observed and measured every 3 days after administration of oncolytic virus.

HCC827 Xenograft Tumor Model in Mice with Humanized Immune System

This experiment was completed by commissioning PharmaLegacy Biomedical Technology (Shanghai) Co., Ltd. The CD34$^+$ humanized mice prepared by PharmaLegacy were used in this experiment. The animals were specific pathogen free (SPF) mice, about 22-23 weeks old, which have been identified as mice with humanized immune system (the proportion of human CD45$^+$ cell was greater than 15%). Each mouse was injected with 2×10$^6$ HCC827 tumor cells on both sides for tumor formation. When the size of tumors on the right side was about 80-100 mm$^3$ and the mice were in a healthy constitution, the mice were randomly divided into four groups, namely vehicle group (virus cryopreservation solution, n=6, intratumoral administration, once every other day, a total of 5 times), positive drug Gemcitabine group (Gemzar® Gemcitabine, n=6, tail vein injection, a dose of 120 mg/kg, once every 4 days, a total of 4 times), positive control PD-1 antibody group (a gift from Lyvgen Biopharma (Shanghai) Co., Ltd., n=6, intraperitoneal injection, a dose of 10 mg/kg, 2 times a week, a total of 6 times) and rAd-IFN-3-SP-E1A(Δ24 bp)-E1B group (n=6, intratumoral administration, a dose of 1.5×10$^{10}$ vp/mouse/time, once every other day, a total of 5 times). Tumors were formed on both sides but only the right side was administered with drugs. The tumor size was observed and measured twice a week.

PDX (Patient Derived Xenograft) Model in Nude Mice

This experiment was completed by commissioning Shanghai Lide Biotech Co., Ltd. The tumor tissues from one case of triple negative breast cancer, one case of lung squamous carcinoma and one case of lung adenocarcinoma were cut into tumor tissues pieces with a size of about 3 mm×3 mm×3 mm (about 50-90 mg) for constructing PDX models. 5-week-old nude mice were inoculated with the tumor pieces subcutaneously. The mice after inoculation were observed and monitored for the tumor growth. When the average tumor volume of tumor-bearing mice reached about 150 mm$^3$, the mice were grouped and administered for observation. Mice in each PDX model were randomly divided into 2 groups with 3 mice in each group. One group was vehicle group (virus cryopreservation solution, intratumor administration, once every other day, a total of 5 times), and the other group is rAd-IFN-1-SP-E1A(Δ24 bp)-E1B group (intratumoral administration, a dose of 1.5×10$^{10}$ vp/mouse/time, once every other day, a total of 5 times). The tumor size was observed and measured twice a week.

III. Single Cell Yield Test in Medium-Scale Production

The subcultured HEK-293 cells were cultured with DMEM medium (containing 10% FBS) for expansion into seventeen T175 culture flasks (purchased from Corning), taking care to keep the cells in each flask evenly distributed. Before virus inoculation, the medium in one T175 culture flask was discarded, and 5 ml of trypsin was added for digestion and then the cells were collected. The cell concentration was determined by a cell counter after appropriate dilution of cells, so that the number of cells in one T175 culture flask at this time point could be calculated. The recombinant oncolytic adenoviruses rAd-IFN-1-SP-E1A (Δ24 bp)-E1B and rAd-IFN-3-SP-E1A(Δ24 bp)-E1B were subjected to VP measurement (HPLC method) for the concentration of virus. Cells in T175 culture flasks were inoculated with one of the two oncolytic adenoviruses to be tested at a virus/cell ratio of 400:1 or 800:1, each group has four flasks for a total of 16 T175 culture flasks, making sure the groups were labeled. After 42 h of culture in a $CO_2$ incubator, cells of two T175 flasks in each group were harvested, and after 54 hours of culture, cells of the remaining two T175 flasks in each group were harvested. Upon harvesting, the culture medium in the flasks was collected as a supernatant sample. Then 5 ml of virus preservation solution was added to each flask, and all the cells were scraped into 15 ml centrifuge tubes as a cell sample. Each cell sample was subjected to three freeze-thaw cycles from −80° C. to room temperature, followed by centrifugation. 2 ml of the supernatant was used for VP measurement. Based on the sum of the VP measurement results of the supernatant sample and the cell sample, the total yield of cells in each group was obtained, which was divided by the number of cells at the time of inoculation to obtain the single cell yield of each group.

Example 1 Construction of Recombinant Oncolytic Adenovirus Carrying Consensus Interferon Gene The structure and construction method of a recombinant oncolytic adenovirus carrying consensus interferon gene are as follows. First, on the back bone of wild-type adenovirus, the 24 base pairs (364-387 bp) of the E1A protein encoding gene responsible for encoding amino acids 122-129 of E1A protein were deleted. After deletion of the above-mentioned fragments, E1A protein cannot bind to Rb protein, which prevents the release of E2F which promotes the host cell to enter cell cycle. The virus undergoing the above modifications can only selective replicate in tumor cells with dysfunctional Rb protein. Then, the wild-type promoter of E1A gene was replaced with a tumor-specific survivin promoter, which further enhances the safety and targeting of the adenovirus. The expression cassette of consensus interferon protein (Infergen) (as shown in SEQ ID NOs: 2, 3 and 4) was inserted into the above-mentioned adenovirus vector to generate a recombinant oncolytic adenovirus carrying the consensus interferon gene rAd-IFN-1-SP-E1A(Δ24 bp)-E1B (containing the expression cassette shown in SEQ ID NO: 2), rAd-IFN-2-SP-E1A(Δ24 bp)-E1B (containing the expression cassette shown in SEQ ID NO: 3), or rAd-IFN-3-SP-E1A(Δ24 bp)-E1B (containing the expression cassette shown in SEQ ID NO: 4).

The above three types of viruses were deposited at China Center for Type Culture Collection (Wuhan, China). The specific deposit information is as follows:

(1) Deposit date: Dec. 12, 2018. Deposit name: Recombinant Human Type 5 Adenovirus rAd-IFN-3-SP-E1A(Δ24 bp)-E1B. Accession number: CCTCC NO: V201871.

(2) Deposit date: Aug. 26, 2019. Deposit name: Recombinant Human Type 5 Adenovirus rAd-IFN-1-SP-E1A(Δ24 bp)-E1B. Accession number: CCTCC NO: V201957.

(3) Deposit date: Aug. 26, 2019. Deposit name: Recombinant Human Type 5 Adenovirus rAd-IFN-2-SP-E1A(Δ24 bp)-E1B. Accession number: CCTCC NO: V201958.

In addition, an no-load virus rAd-SP-E1A(Δ24 bp)-E1B without rIFN expression cassette was also constructed as a control. The structure of the above virus constructs are shown in FIG. 1.

Example 2 Expression Level and Function Analysis of Target Protein of Recombinant Oncolytic Adenoviruses In order to compare the expression ability of the recombinant oncolytic adenoviruses carrying different consensus interferon expression cassettes constructed in Example 1, that is, the ability to express the consensus interferon rIFN protein, the human breast cancer cell line MDA-MB-231 cells were infected with 10 MOI rAd-IFN-1-SP-E1A(Δ24 bp)-E1B, rAd-IFN-2-SP-E1A(Δ24 bp)-E1B, and rAd-IFN-3-SP-E1A(Δ24 bp)-E1B, respectively. After 24 hours of infection, cells were lysed to collect protein samples for Western Blotting analysis.

Figure 2:
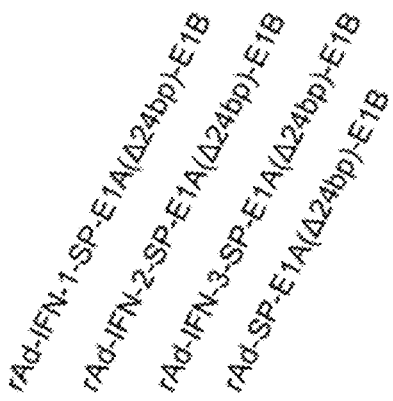
FIG. 2 shows the in vitro expression of the target protein carried by each oncolytic adenovirus of the present disclosure.
Figure 2:
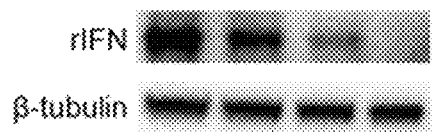

The results are shown in FIG. 2. All recombinant oncolytic viruses carrying rIFN coding sequence can express the target protein rIFN, while the no-load virus had no detectable rIFN protein band, indicating that the recombinant oncolytic viruses constructed in Example 1 can function normally in cells. In addition, it can be seen from FIG. 2 that the recombinant oncolytic adenovirus rAd-IFN-1-SP-E1A (Δ24 bp)-E1B has the highest level of expressing the exogenous therapeutic gene rIFN, followed by rAd-IFN-2-SP-E1A (Δ24 bp)-E1B, while rAd-IFN-3-SP-E1A(Δ24 bp)-E1B has the lowest expression level, which suggested that the difference in the coding sequence of the target protein affects the expression of the target protein.

Next, whether the rIFN protein expressed by viruses has normal functions was tested. Since interferon can up-regulate the expression of type I major histocompatibility complex (MHC I, also known as HLA-ABC), the change in the expression of MHC I was employed as a standard to compare the functions of the exogenous recombinant interferon rIFN expressed by each recombinant oncolytic adenovirus.

Figure 3:
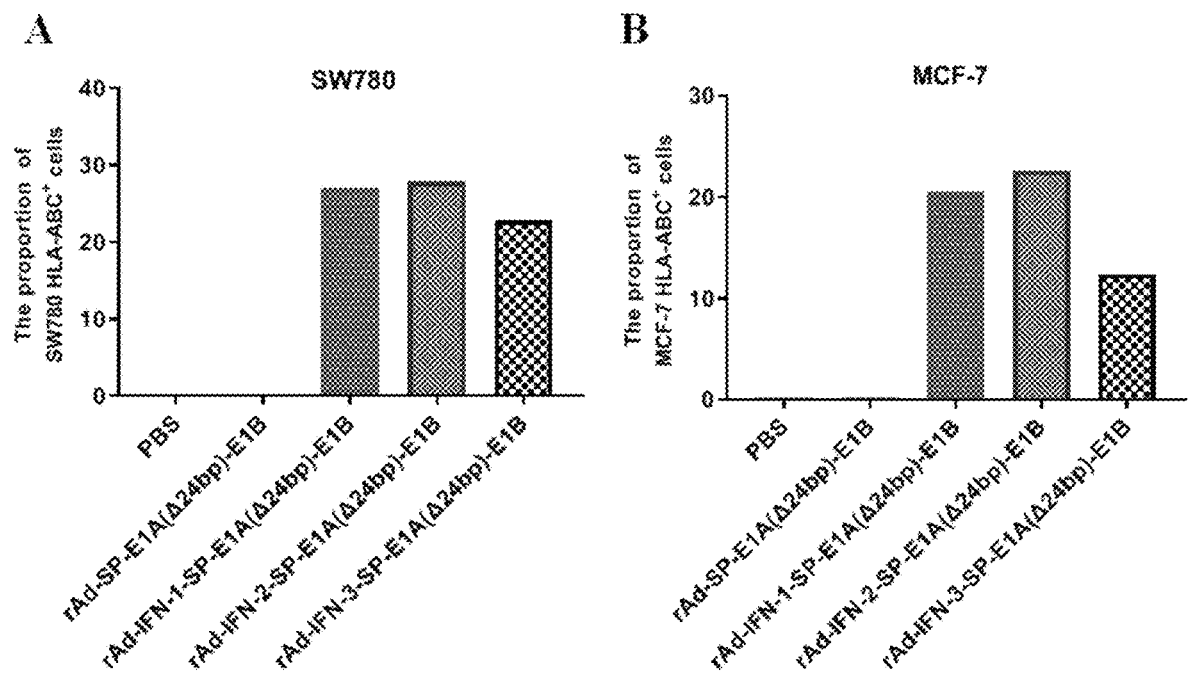

The human bladder cancer SW780 cells were infected with 1 MOI recombinant oncolytic adenoviruses rAd-IFN-1-SP-E1A(Δ24 bp)-E1B, rAd-IFN-2-SP-E1A(Δ24 bp)-E1B and rAd-IFN-3-SP-E1A(Δ24 bp)-E1B respectively. After 24 hours of infection, cells were collected and then stained for flow cytometry analysis. The results are shown in FIG. 3. The expression of MHC I was almost undetectable in the PBS group and the no-load virus rAd-SP-E1A(Δ24 bp)-E1B group, while all recombinant oncolytic adenoviruses capable of expressing rIFN were able to significantly up-regulate MHC I expression, indicating that rIFN expressed by the recombinant oncolytic adenovirus has normal activity (FIG. 3A). Furthermore, rAd-IFN-1-SP-E1A(Δ24 bp)-E1B and rAd-IFN-2-SP-E1A(Δ24 bp)-E1B can up-regulate the expression of MHC I more significantly than rAd-IFN-3-SP-E1A(Δ24 bp)-E1B. The same results were obtained in the human breast cancer cell line MCF-7 (FIG. 3B).

Example 3 Tumor Targeting Test of Recombinant Oncolytic Adenoviruses

As described in Example 1, the all three recombinant oncolytic adenoviruses had undergone replication-targeted modification to replicate only in tumor cells. The effectiveness of targeting tumor cells for replication is closely related to the actual clinical therapeutic effect of oncolytic viruses. In this example, the replication ability of each recombinant oncolytic adenovirus in the breast cancer cell line MDA-MB-231 and normal breast cell line MCF-10A was tested.

In this example, the replication ability of a virus was measured by "virus replication ratio" and "targeting replication coefficient". "Virus replication ratio" refers to a ratio of the number of progeny viruses produced by host cells after being infected with the oncolytic adenovirus for a certain period of time to the number of the original virus for infection, which is used to quantitatively represent the replication ability of an oncolytic adenovirus in the host cell. "Targeting replication coefficient" refers to a ratio of the virus replication ratio of an oncolytic adenovirus in tumor cells to the virus replication ratio of the same oncolytic adenovirus in normal cells, which is used to quantitatively represent the tumor-targeting replication of an oncolytic adenovirus.

Specifically, 1 MOI of each recombinant oncolytic adenovirus was used to infect host cells. After 72 hours of infection, progeny virus was collected and the titer was determined. The virus replication ratio was obtained by dividing the progeny virus titer with the original infection titer. The targeting replication coefficient was calculated from the virus replication ratios of each virus in tumor cells and normal cells.

Figure 4:
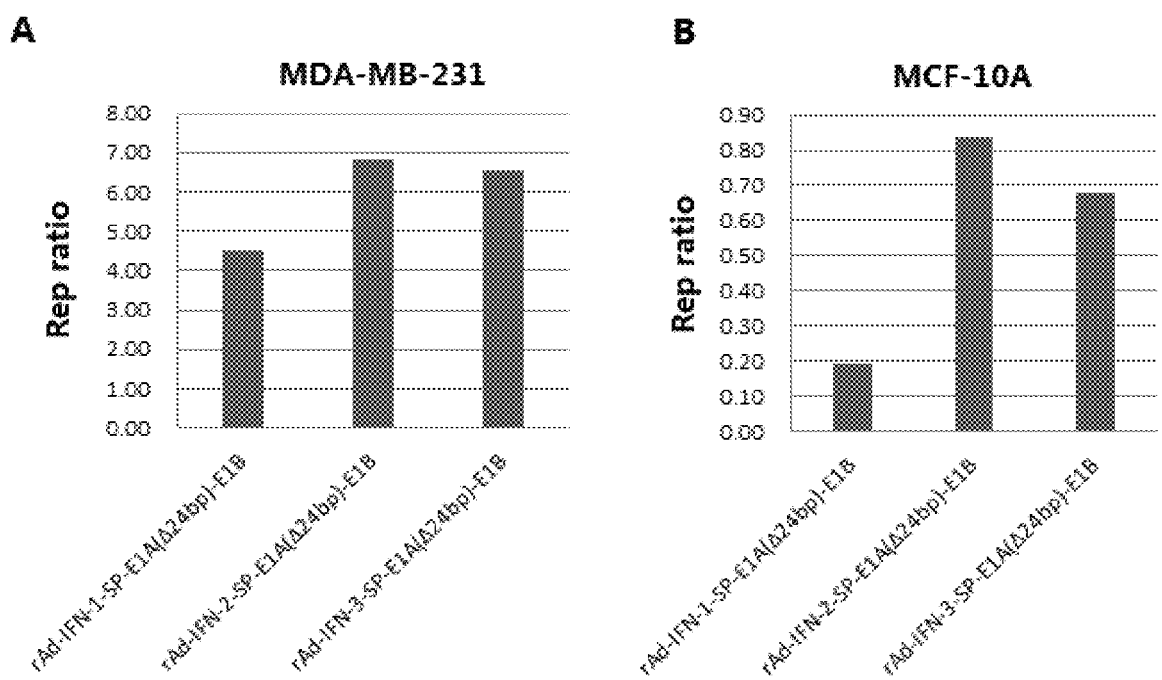
FIG. 4 shows the virus replication ratio of each oncolytic adenovirus of the present disclosure in breast cancer cell line MDA-MB-231 (4A) and normal breast cell line MCF-10A (4B).

The results are shown in Table 1 and FIG. 4. The three recombinant oncolytic adenoviruses were able to produce more in the cancer cell line MDA-MB-231, with high virus replication ratio, and the virus replication ratios of rAd-IFN-2-SP-E1A(Δ24 bp)-E1B and rAd-IFN-3-SP-E1A(Δ24 bp)-E1B were slightly higher than that of rAd-IFN-1-SP-E1A (Δ24 bp)-E1B. However, in the normal cell line MCF-10A, the virus replication ratios of all three recombinant oncolytic adenoviruses were low, and the virus replication ratio of rAd-IFN-1-SP-E1A(Δ24 bp)-E1B was the lowest, which indicated that the three recombinant oncolytic adenoviruses had poor replication ability in normal cells. Though rAd-IFN-1-SP-E1A(Δ24 bp)-E1B had a slightly lower virus replication ratio in the breast cancer cell line MDA-MB-231 than rAd-IFN-2-SP-E1A(Δ24 bp)-E1B and rAd-IFN-3-SP-E1A(Δ24 bp)-E1B, due to its significantly lower virus replication ratio in the normal breast cells MCF-10A, rAd-IFN-1-SP-E1A(Δ24 bp)-E1B had the highest targeting replication coefficient of 23.36, which was much higher than the other two recombinant oncolytic adenoviruses. That is to say, rAd-IFN-1-SP-E1A(Δ24 bp)-E1B had the best tumor cell targeting and the highest safety among them.

TABLE 1

| Targeting replication coefficient of each recombinant oncolytic adenovirus | |
|---|---|
| Virus name | Targeting replication coefficient |
| rAd-IFN-1-SP-E1A(Δ24bp)-E1B | 23.36 |
| rAd-IFN-2-SP-E1A(Δ24bp)-E1B | 8.15 |
| rAd-IFN-3-SP-E1A(Δ24bp)-E1B | 9.64 |

Example 4 Recombinant Oncolytic Adenovirus can Specifically Kill Cancer Cells

Figure 5:
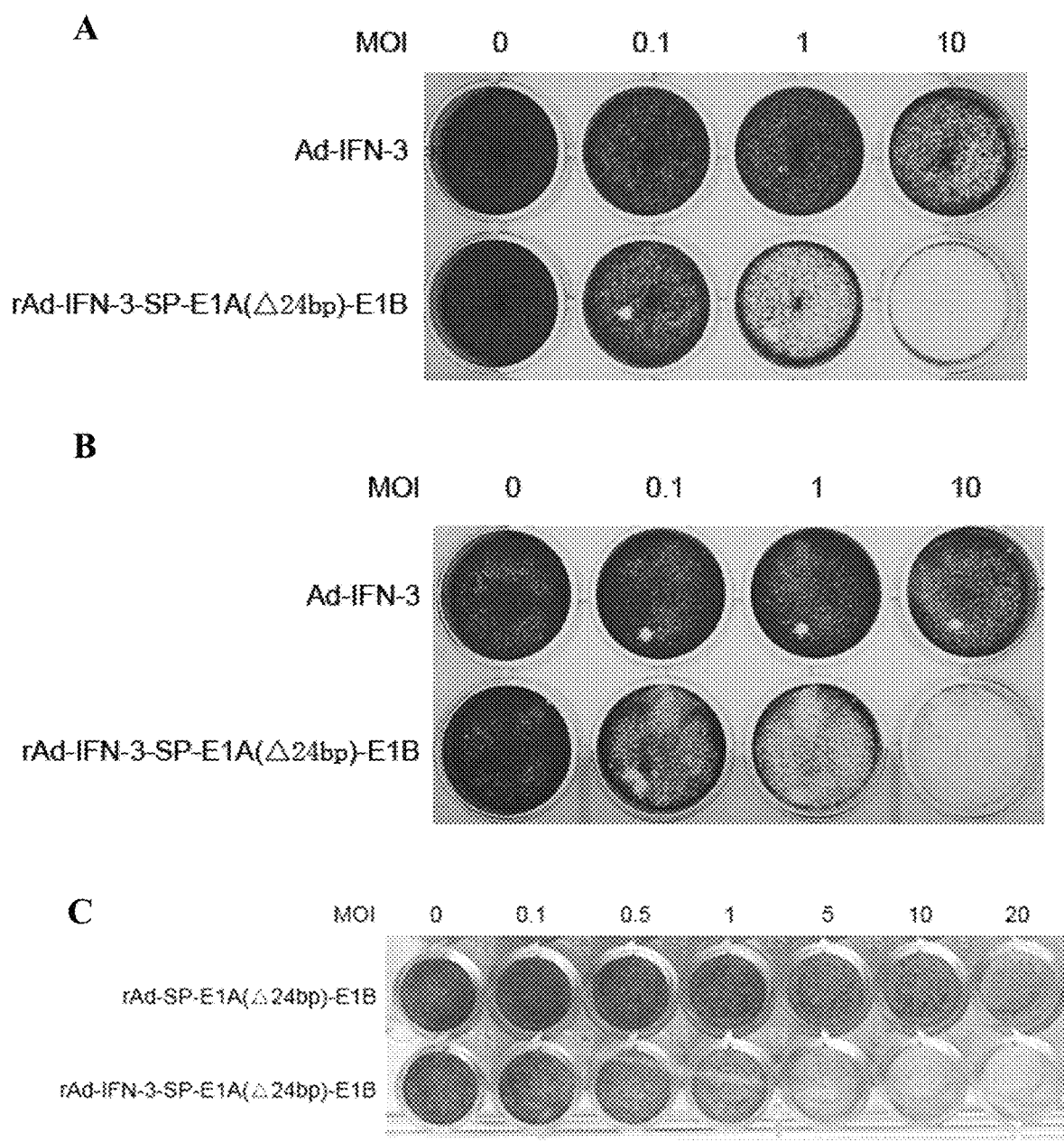
Figure 5:
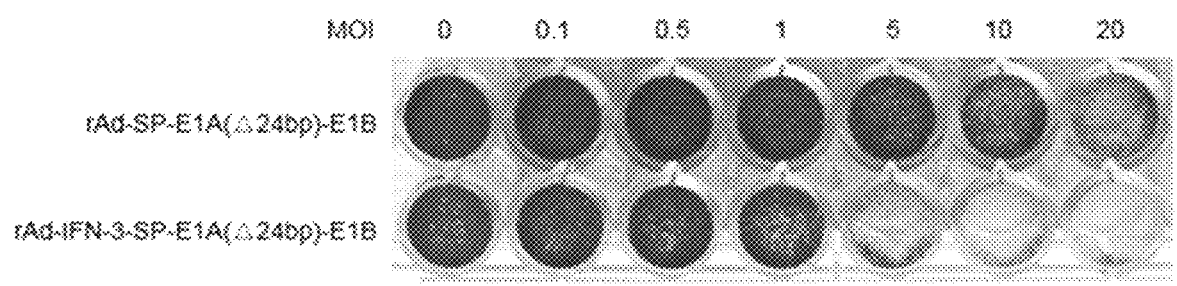
Figure 5:
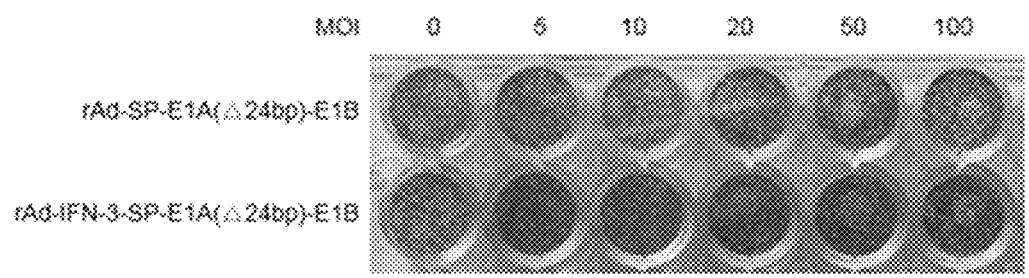

In this example, the recombinant oncolytic adenovirus rAd-IFN-3-SP-E1A(Δ24 bp)-E1B with a moderate targeting replication coefficient verified in Example 2 was used as an example to study the effect of the recombinant oncolytic adenovirus of the present disclosure on cancer cells and normal cells (FIG. 5). In this example, a non-replicative adenovirus was constructed by deleting the E1 region as a control, and a non-replicative recombinant adenovirus carrying IFN-3 gene, Ad-IFN-3, was constructed by inserting the IFN-3 expression cassette into the vector (see FIG. 1).

In the liver cancer cell line Huh-7, the killing effects of rAd-IFN-3-SP-E1A(Δ24 bp)-E1B and Ad-IFN-3 were studied. As shown in FIG. 5A, rAd-IFN-3-SP-E1A(Δ24 bp)-E1B had a significantly stronger ability to kill liver cancer cells than the non-replicative virus Ad-IFN-3. 1 MOI rAd-IFN-3-SP-E1A(Δ24 bp)-E1B can kill more than half of Huh-7 cells, which was superior to 10 MOI Ad-IFN-3.

In the colon cancer cell line SW620, the killing effects of replicative and non-replicative oncolytic adenoviruses were compared. As shown in FIG. 5B, rAd-IFN-3-SP-E1A(Δ24 bp)-E1B had a significantly stronger ability to kill the colon cancer cell line SW620 than the non-replicative virus Ad-IFN-3. 0.1 MOI rAd-IFN-3-SP-E1A(Δ24 bp)-E1B can kill about half of SW620 cells, which was superior to 10 MOI Ad-IFN-3.

In this example, the killing effect of oncolytic adenovirus carrying or not carrying interferon sequence on cancer cells was further compared. As shown in FIG. 5C, rAd-IFN-3-SP-E1A(Δ24 bp)-E1B had a significantly stronger ability to kill the breast cancer cell line MDA-MB-231 than the no-load control virus rAd-SP-E1A(Δ24 bp)-E1B. 0.5 MOI rAd-IFN-3-SP-E1A(Δ24 bp)-E1B can kill about half of MDA-MB-231 cells, basically the same as 5 MOI rAd-SP-E1A(Δ24 bp)-E1B.

In the lung cancer cell line HCC827, the killing effects of rAd-IFN-3-SP-E1A(Δ24 bp)-E1B and the no-load control virus rAd-SP-E1A(Δ24 bp)-E1B were compared. As shown in FIG. 5D, the results showed that rAd-IFN-3-SP-E1A(Δ24 bp)-E1B had a significantly stronger ability to kill the lung cancer HCC827 cells than the no-load control virus rAd-SP-E1A(Δ24 bp)-E1B. 5 MOI rAd-IFN-3-SP-E1A(Δ24 bp)-E1B can kill almost all HCC827 cells, stronger than the effect of 20 MOI rAd-SP-E1A(Δ24 bp)-E1B.

On the contrary, for the normal cell human liver fibroblast cell line HLF, as shown in FIG. 5E, the recombinant oncolytic adenovirus rAd-IFN-3-SP-E1A(Δ24 bp)-E1B and the corresponding no-load control virus showed no killing effect on HLF cells.

The above results indicated that the recombinant oncolytic adenovirus of the present disclosure can specifically kill tumor cells with minimal effect on normal cells, and thus has good safety.

Figure 6:
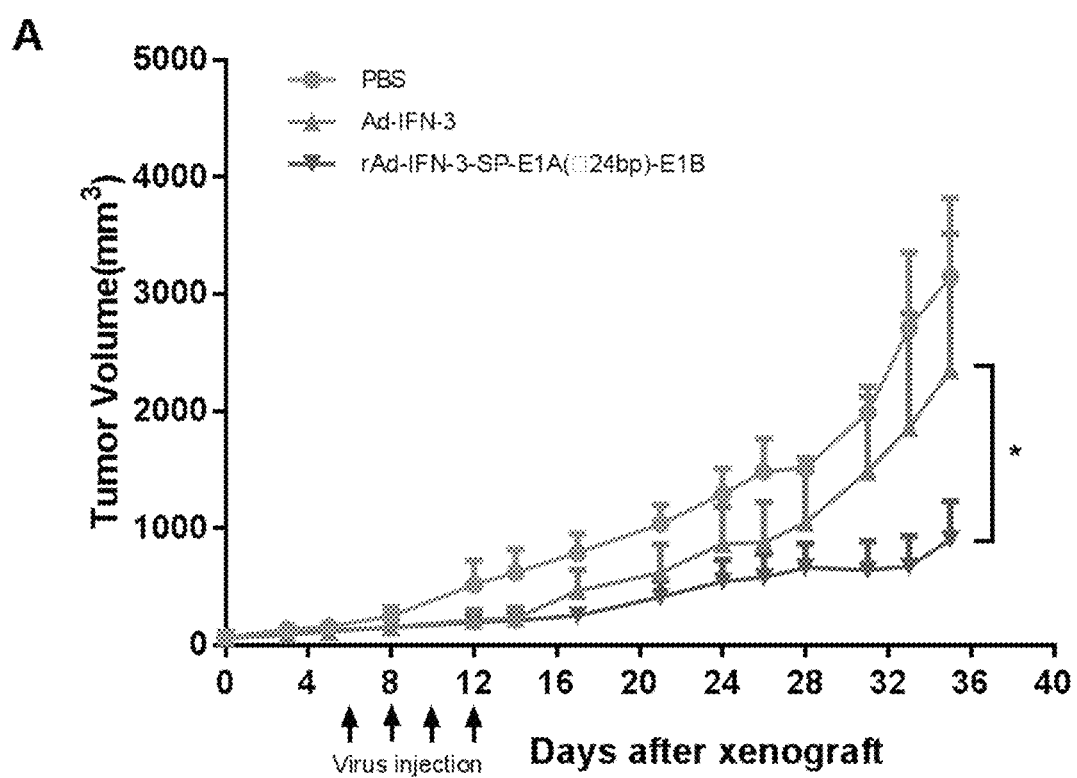
Figure 6:
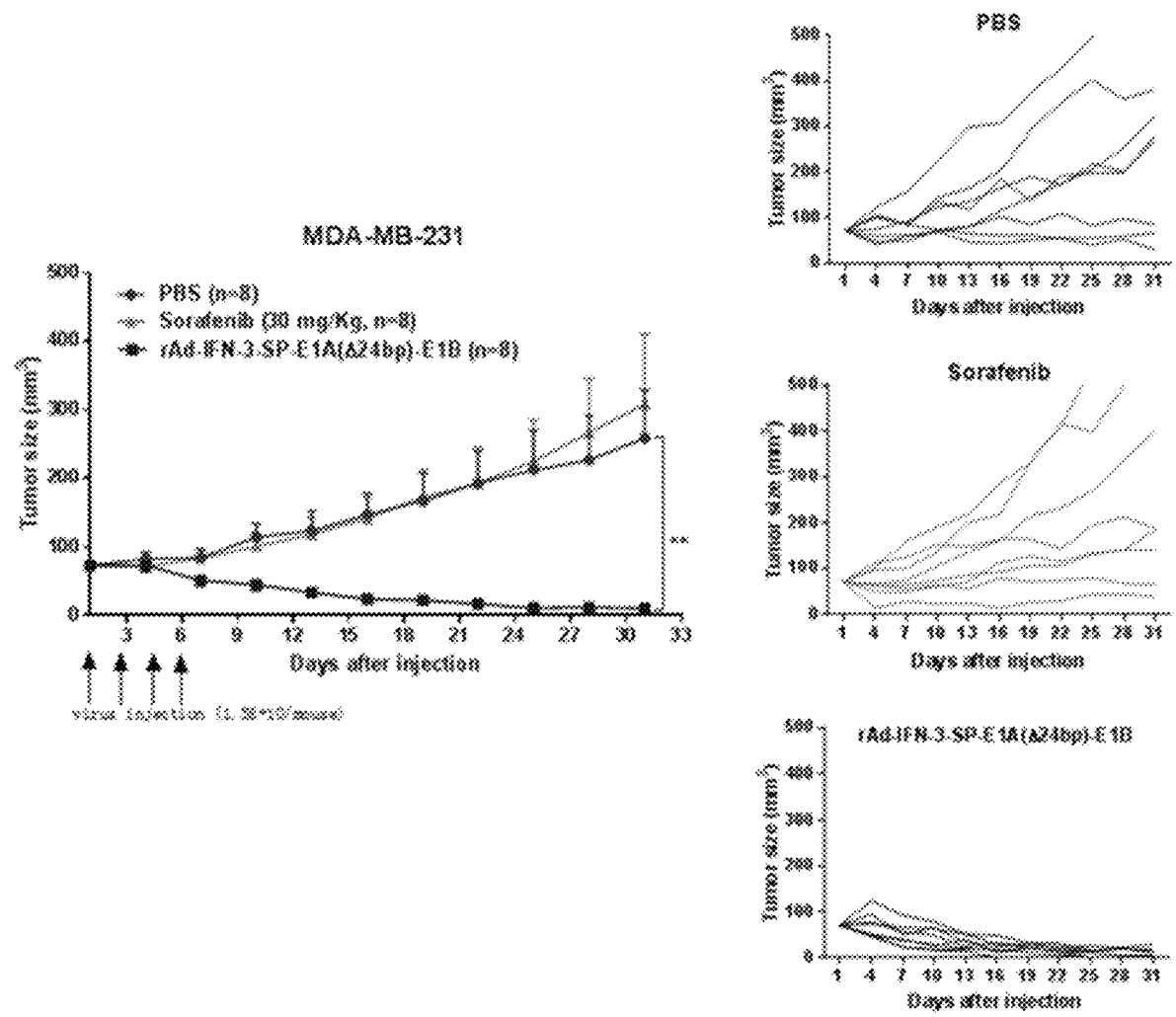
Figure 6:
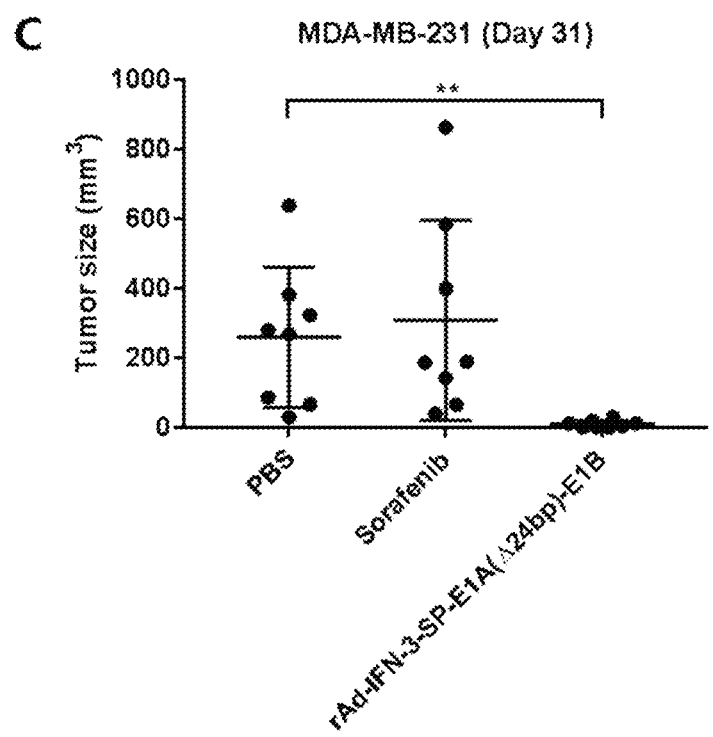
Figure 6:
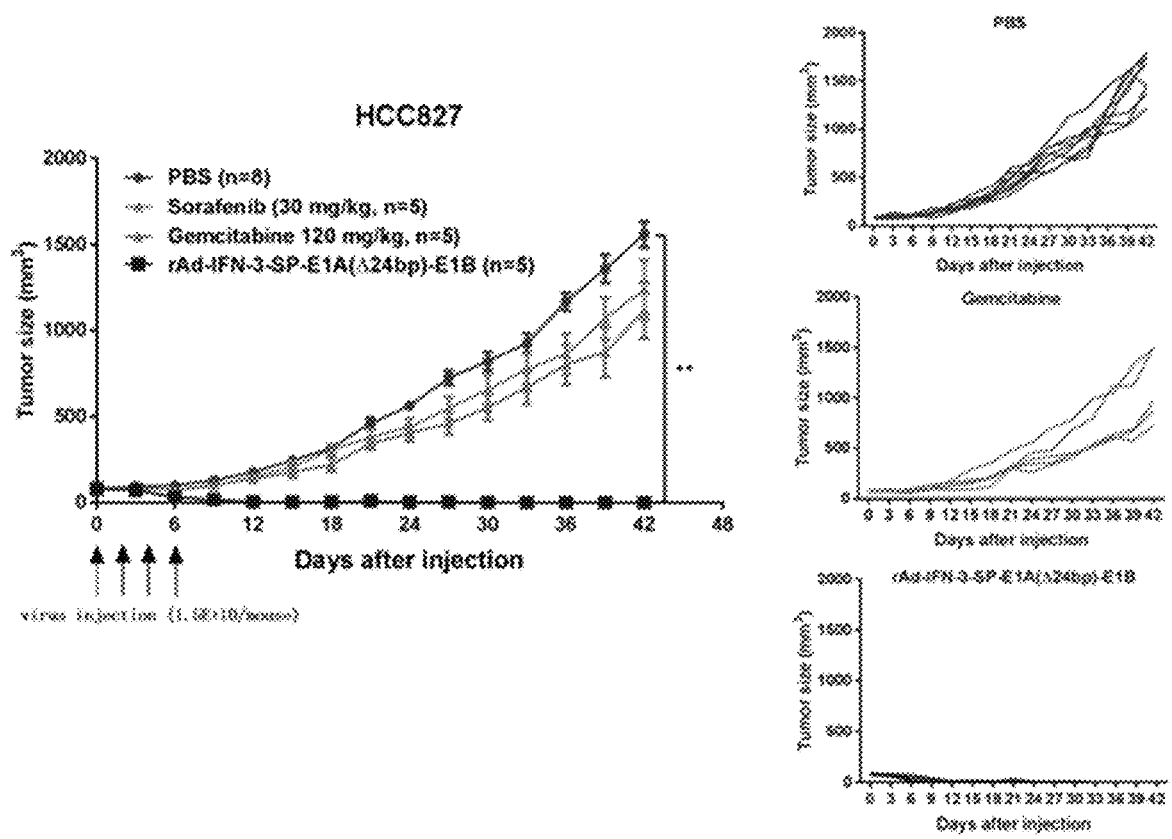
Figure 6:
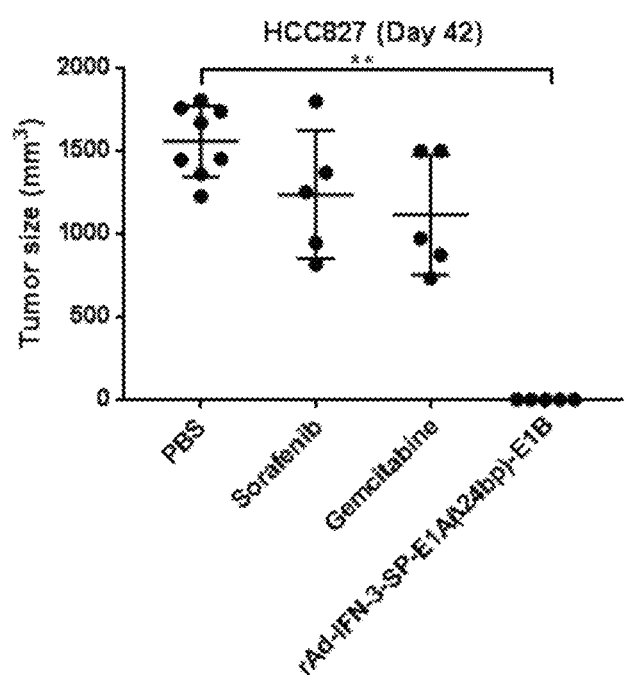

Example 5 Recombinant Oncolytic Adenovirus Significantly Inhibits the Growth of Xenograft Tumor in Nude Mice In this example, the inhibitory effect of rAd-IFN-3-SP-E1A(Δ24 bp)-E1B on SW620 xenograft tumor in nude mice was tested (FIG. 6). As shown in FIG. 6A, the recombinant oncolytic adenovirus rAd-IFN-3-SP-E1A(Δ24 bp)-E1B also showed significantly better drug efficacy than the non-replicative adenovirus carrying IFN-3 gene Ad-IFN-3 in SW620 xenograft tumor in nude mouse.

The effect of the recombinant oncolytic adenovirus rAd-IFN-3-SP-E1A(Δ24 bp)-E1B in the MDA-MB-231 xenograft tumor in nude mouse was further tested. As shown in FIGS. 6B and 6C, the recombinant oncolytic adenovirus showed excellent drug efficacy with almost all of the xenograft tumors being eliminated, and the tumor inhibition rate was up to 96.4%.

Also, the effect of the recombinant oncolytic adenovirus rAd-IFN-3-SP-E1A(Δ24 bp)-E1B in the HCC827 xenograft tumor model in nude mouse was tested. As shown in FIGS. 6D and 6E, the recombinant oncolytic adenovirus showed excellent drug efficacy with all of the xenograft tumors being eliminated, which was significantly superior to the positive control drugs sorafenib and gemcitabine, and the tumor inhibition rate reached 100%.

Figure 7:
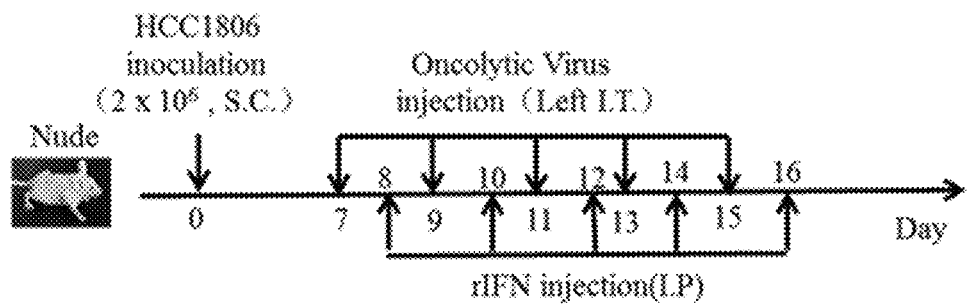
Figure 7:
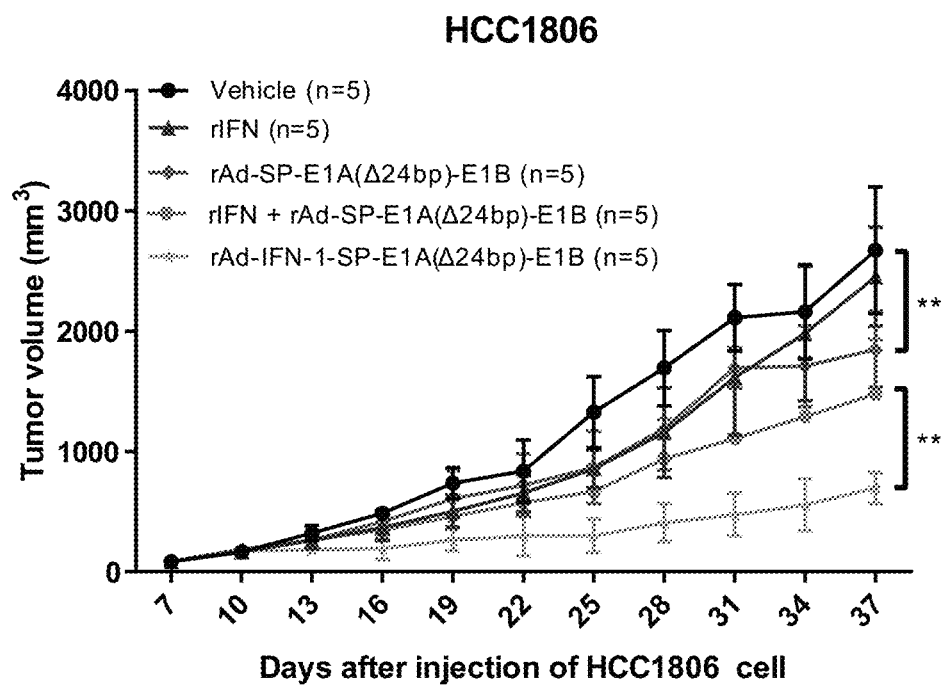

Example 6 Recombinant Oncolytic Adenoviruses Show Synergistic Inhibitory Effect on Tumors In this example, it was verified that the recombinant oncolytic adenovirus of the present disclosure (rAd-IFN-1-SP-E1A(Δ24 bp)-E1B) can achieve better results than rIFN protein alone, no-load oncolytic virus alone, or a combination of rIFN protein and no-load oncolytic virus (FIG. 7), which indicated that the recombinant oncolytic virus with the structure of the present disclosure can achieve unexpected synergistic effect.

Specifically, the triple negative breast cancer cell line HCC1806 xenograft tumor of nude mice with less immune cell infiltration were used for in vivo drug efficacy testing. Each nude mouse was injected subcutaneously with $2 \times 10^6$ HCC1806 cells for subcutaneous tumor formation. When the tumor volume reached about 90 mm$^3$, mice were randomly divided into groups and administered. The dosage regimen is shown in FIG. 7A. vehicle control and each recombinant oncolytic adenovirus were administered to mice on the day of grouping by intratumoral injection at a dose of $1.5 \times 10^{10}$ VP/time/mouse (50 µL/time/mouse), once every other day for a total of five times. Recombinant interferon protein was administered to mice on the second day of grouping by intraperitoneal injection at a dose of 20 µg/time/mouse, once every other day for a total of five times. The tumor size was measured every three days.

The results are shown in FIG. 7B. Compared with the negative control vehicle, the administration of recombinant interferon protein alone had no obvious tumor-suppressive effect. In contrast, the administration of no-load oncolytic adenovirus alone can produce a certain tumor-suppressive effect. If recombinant interferon protein was further used in combination with no-load oncolytic adenovirus, a stronger tumor-suppressive effect can be obtained than using any of them alone. However, the recombinant oncolytic adenovirus rAd-IFN-1-SP-E1A(Δ24 bp)-E1B of the present disclosure showed a best tumor-suppressive effect, which had an extremely significant difference statistically compared with a combination of the two (**). The above results indicated that the recombinant oncolytic adenovirus carrying rIFN therapeutic gene constructed by the present disclosure exhibits a synergistic effect.

Figure 8:
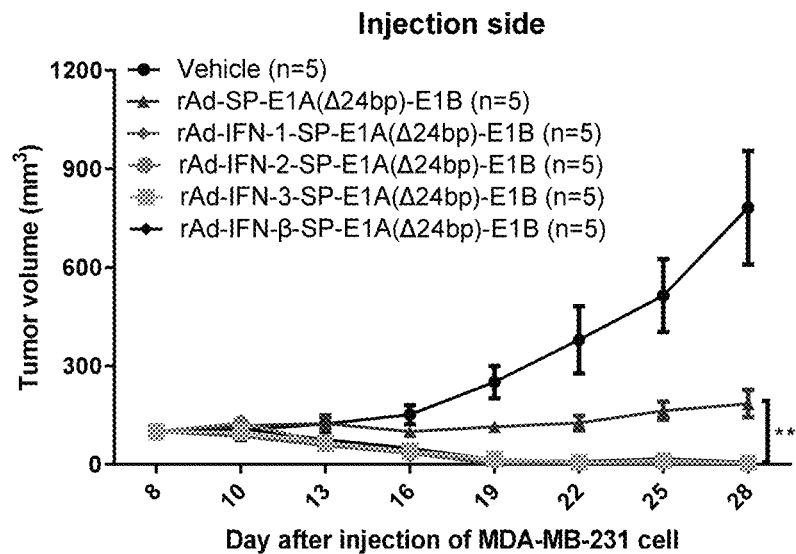
Figure 8:
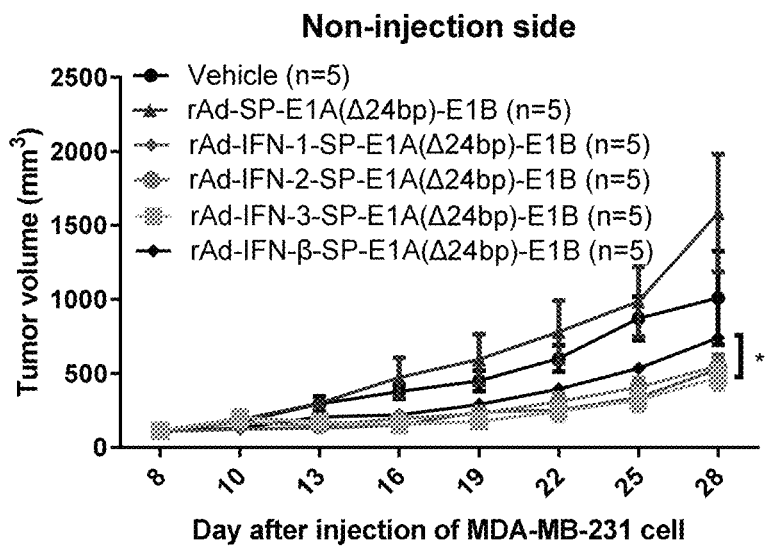

Example 7 Recombinant Oncolytic Adenoviruses Show Overall Inhibitory Effect on Tumors In Vivo In this example, it was found that the inhibition of the recombinant oncolytic adenovirus on tumor in vivo was not limited to the injection site, but also with a surprising effect at the non-injection site (FIG. 8).

Specifically, the triple negative breast cancer cell line MDA-MB-231 xenograft tumor model in nude mouse was employed. A recombinant oncolytic adenovirus rAd-IFN-β-SP-E1A(Δ24 bp)-E1B carrying natural IFN-β was constructed as a control for drug effect. Each nude mouse was injected with $2 \times 10^6$ MDA-MB-231 cells on left and right sides to form subcutaneous tumors on both sides. When volume of the tumor on the left side reached about 90 mm$^3$, mice were randomly divided into groups and administered. Vehicle control and each recombinant oncolytic adenovirus were administered on the left side tumor on the day of grouping by intratumoral injection at a dose of $1.5 \times 10^{10}$ VP/time/mouse (50 µL/time/mouse), once every other day for a total of five times, while the tumor on the right side was not treated. The size of tumors on both sides were measured every three days.

For the tumor on administration side (left side), as shown in FIG. 8A, by the end of the experiment, all recombinant oncolytic adenoviruses carrying interferon gene can almost completely eliminate xenograft tumors, and the no-load oncolytic adenoviruses also showed a significant inhibitory effect on the growth of xenograft tumors. As further shown in Table 2, on the 11th day of administration (i.e., Day 19 in FIG. 8A and Table 2), none of the xenograft tumors in the negative control vehicle group, no-load oncolytic adenovirus rAd-SP-E1A(Δ24 bp)-E1B group or recombinant oncolytic adenovirus rAd-IFN-3-SP-E1A(Δ24 bp)-E1B group was eliminated, 40% of the xenograft tumors in the recombinant oncolytic adenovirus rAd-IFN-2-SP-E1A(Δ24 bp)-E1B group and the recombinant oncolytic adenovirus carrying natural IFN-β, rAd-IFN-β-SP-E1A(Δ24b)-E1B group were eliminated, and all of the xenograft tumors in the recombinant oncolytic adenovirus rAd-IFN-1-SP-E1A(Δ24 bp)-E1B group were eliminated. At the end of the experiment, only in the recombinant oncolytic adenovirus rAd-IFN-1-SP-E1A(Δ24 bp)-E1B group and rAd-IFN-2-SP-E1A (Δ24 bp)-E1B group, all xenograft tumors were eliminated. It can be seen from the above that among these recombinant oncolytic adenoviruses, rAd-IFN-1-SP-E1A(Δ24 bp)-E1B had the fastest effect and the best tumor-suppressive effect. rAd-IFN-2-SP-E1A(Δ24 bp)-E1B showed similar effects, completely eliminating tumor.

TABLE 2

Number of mice (tumor free) in each treatment group on Day 19 and Day 28

| Group | Tumor free on Day 19 | Tumor free on Day 28 |
|---|---|---|
| Vehicle | 0/5 | 0/5 |
| rAd-SP-E1A(Δ24bp)-E1B | 0/5 | 0/5 |
| rAd-IFN-1-SP-E1A(Δ24bp)-E1B | 5/5 | 5/5 |
| rAd-IFN-2-SP-E1A(Δ24bp)-E1B | 2/5 | 5/5 |
| rAd-IFN-3-SP-E1A(Δ24bp)-E1B | 0/5 | 4/5 |
| rAd-IFN-B-SP-E1A(Δ24bp)-E1B | 2/5 | 4/5 |

For the tumor on no administration side (right side), as shown in FIG. 8B, the no-load oncolytic adenovirus had no tumor-suppressive effect at all, and the recombinant oncolytic adenovirus carrying natural IFN-β, rAd-IFN-β-SP-E1A (Δ24 bp)-E1B had a certain tumor-suppressive effect. Compared with rAd-IFN-β-SP-E1A(Δ24 bp)-E1B, the three recombinant oncolytic viruses rAd-IFN-1-SP-E1A(Δ24 bp)-E1B, rAd-IFN-2-SP-E1A(Δ24 bp)-E1B, and rAd-IFN-3-SP-E1A(Δ24 bp)-E1B constructed in the present disclosure produced significantly better tumor-suppressive effects with statistically significant differences (*). There is no obvious difference in drug efficacy between the above three recombinant oncolytic adenoviruses.

It can be seen that the recombinant oncolytic viruses of the present disclosure can kill tumor cells not limited to the local injection site but also non-injection site, which gives immeasurable value for the clinical treatment of cancer, such as for the treatment of tumor metastasis.

Figure 9:
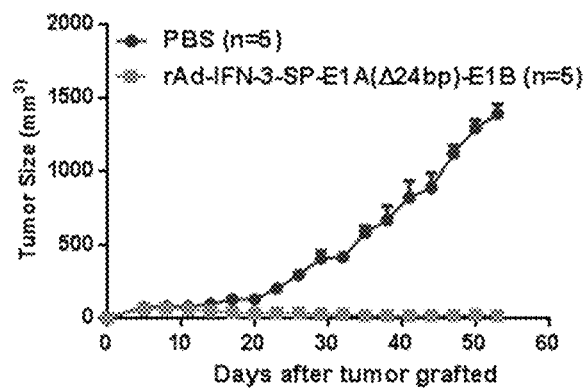
Figure 9:
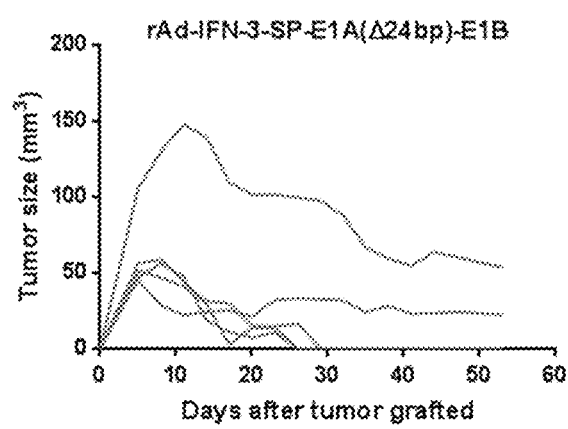
Figure 9:
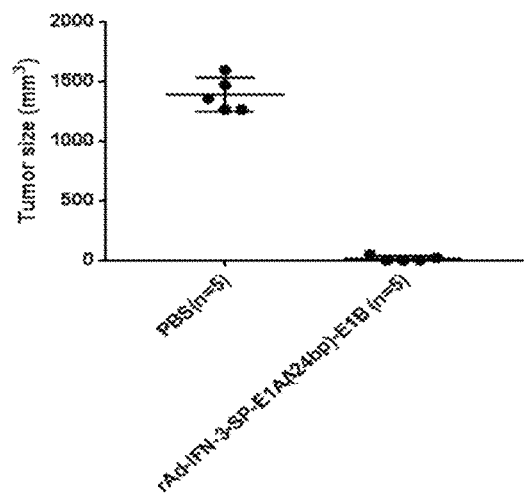

Example 8 Recombinant Oncolytic Adenoviruses Effectively Prevent Tumor Recurrence In order to investigate the duration of the therapeutic effect of the oncolytic adenoviruses of the present disclosure, the mice in which the HCC827 xenograft tumors have been completely regressed by intratumoral injection of rAd-IFN-3-SP-E1A(Δ24 bp)-E1B in Example 5 were employed. The mice were again injected with $2 \times 10^6$ HCC827 tumor cells for tumor formation on one side. In the control group, untreated nude mice of the same age were also injected with $2 \times 10^6$ HCC827 tumor cells for tumor formation on one side. After tumor formation, the mice in these two groups were not treated any more, and the tumor volume was measured twice a week. As shown in FIG. 9, compared with the control group, the growth of the xenograft tumor in the experimental group was significantly inhibited., The tumors only grow to an average volume of less than 100 mm$^3$, and then began to be eliminated until disappear again. The above results indicated that the mice treated with rAd-IFN-3-SP-E1A(Δ24 bp)-E1B had obvious immune memory, which can quickly recognize the same type of tumor cells that appeared in the later stage, showing a good effect of preventing tumor recurrence.

Example 9 Recombinant Oncolytic Adenovirus rAd-IFN-3-SP-E1A(Δ24 bp)-E1B Significantly Inhibits the Growth of Xenograft Tumors in Humanized Mice In order to further investigate the tumor-suppressive effect of the recombinant oncolytic adenovirus in an environment more similar to human immune environment, in this example, the tumor-suppressive effect of the recombinant oncolytic adenovirus of the present disclosure on xenograft tumors of mice with humanized immune system was tested. rAd-IFN-3-SP-E1A(Δ24 bp)-E1B was selected for test in this example. Mice with humanized immune system were injected subcutaneously on both sides with human HCC827 cells for formation of xenografts. The recombinant oncolytic adenoviruses were administered to the tumor on the right side only, while no treatment on the left side.

Figure 10:
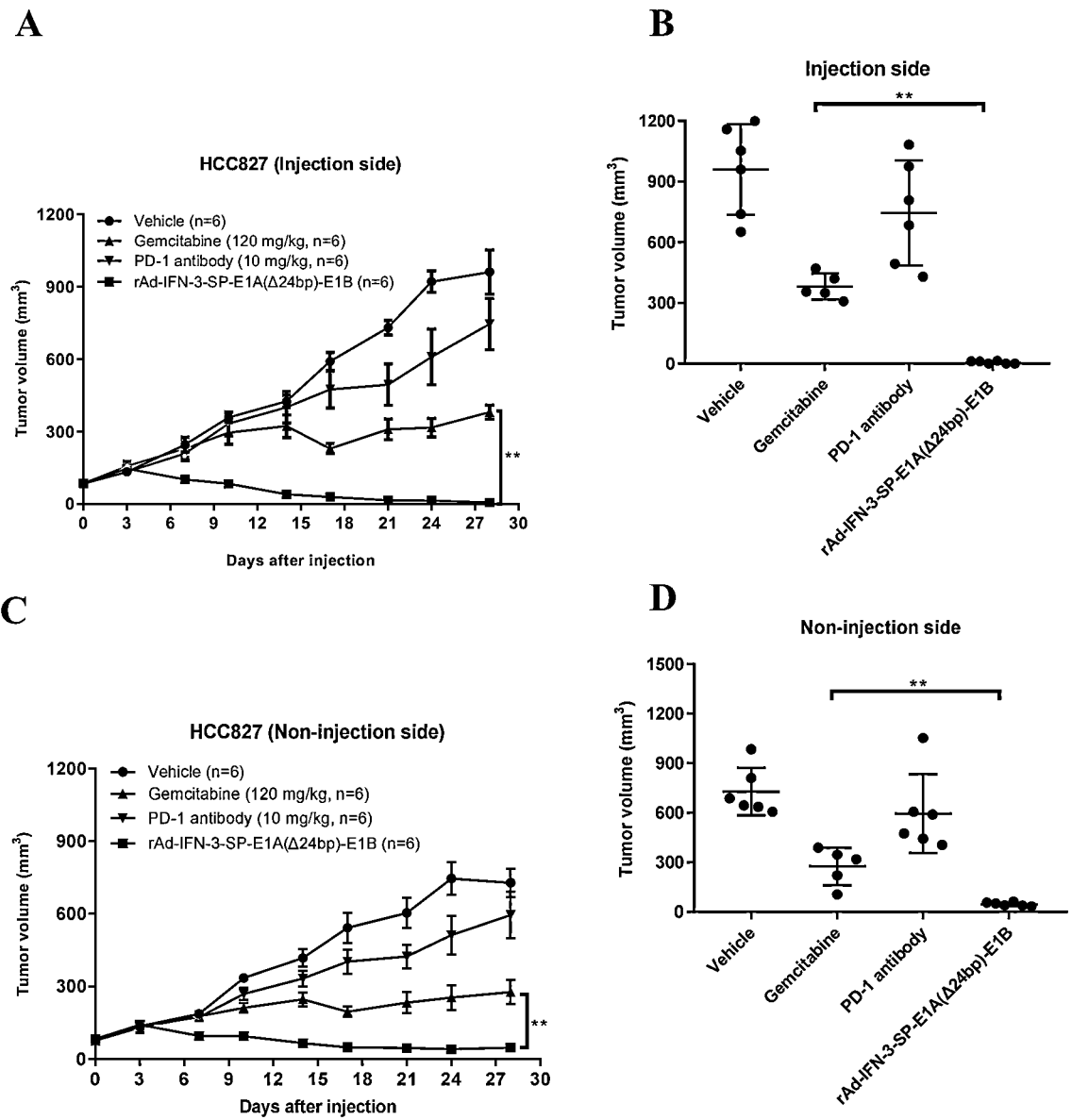

The results are shown in FIG. 10. The xenograft tumor on the right side (administration side) in the test group began to gradually shrink after intratumoral injection of recombinant oncolytic adenovirus rAd-IFN-3-SP-E1A(Δ24 bp)-E1B, and the tumor inhibition rate reached 96.4% at the end of the experiment, which was significantly better than the positive control drug gemcitabine and PD-1 antibody (FIGS. 10A and 10B). Similar to the results of Example 7, the xenograft tumors on the left side (no administration side) in the test group also began to gradually shrink after intratumoral administration on the right side, and the tumor inhibition rate reached 92.5% at the end of the experiment, which was also significant better than the positive control drug gemcitabine and PD-1 antibody (FIGS. 10C and 10D). The results indicated that in an environment similar to the human body, which is complicated, the recombinant oncolytic adenovirus rAd-IFN-3-SP-E1A(Δ24 bp)-E1B still exhibits excellent tumor killing effect not limited to the local injection site, giving an immeasurable clinical application value.

Example 10 Recombinant Oncolytic Adenovirus rAd-IFN-1-SP-E1A(Δ24 bp)-E1B Significantly Inhibits the Growth of PDX Xenograft Tumor in Nude Mice In order to further investigate the tumor-suppressive effect of the recombinant oncolytic adenovirus in an environment more similar to the patients (considering tumors have a strong heterogeneity), in this example, the tumor-suppressive effect of the recombinant oncolytic adenovirus of the present disclosure in patient-derived xenograft (PDX) model of nude mouse was tested. rAd-IFN-1-SP-E1A(Δ24 bp)-E1B was selected for test in this example. One case of lung adenocarcinoma, one case of lung squamous cell carcinoma, and one case of triple negative breast cancer were used for PDX tests.

Figure 11:
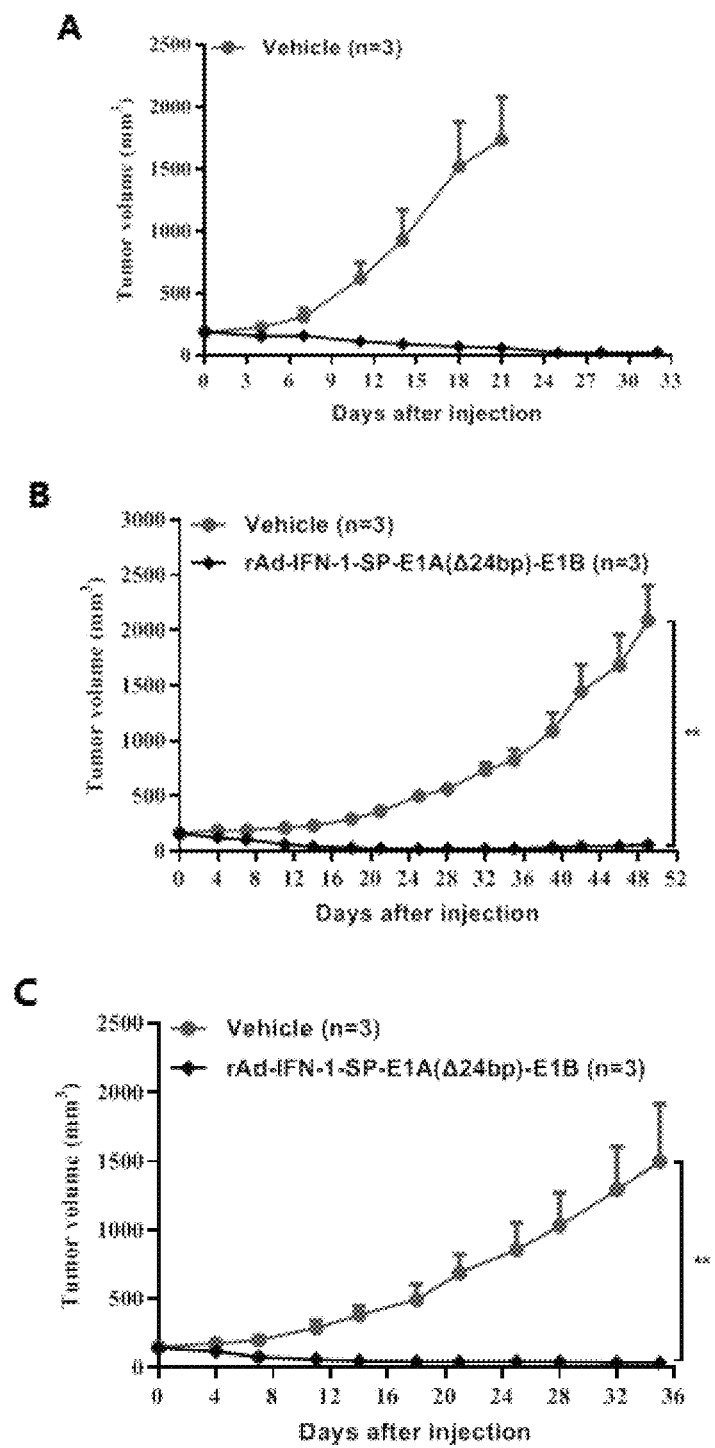

The results are shown in FIG. 11. The recombinant oncolytic adenovirus rAd-IFN-1-SP-E1A(Δ24 bp)-E1B showed excellent tumor killing effects on lung adenocarcinoma PDX (FIG. 11A), lung squamous cell carcinoma PDX (FIG. 11B) and triple negative breast cancer PDX (FIG. 11C) model, with tumor inhibition rates of 98.7%, 97.0%, and 97.5%, respectively, at the end of the experiment. The results indicated that the recombinant oncolytic adenovirus rAd-IFN-1-SP-E1A(Δ24 bp)-E1B still exhibits excellent tumor killing effect for treating highly heterogeneous tumors of clinical origin.

Example 11 Single Cell Yield Test of the Recombinant Oncolytic Adenovirus in Medium-Scale Production To be used as a drug, the recombinant oncolytic adenovirus needs to be fermented by large-scale production. The single cell yield in medium-scale production is not only a basis for evaluating whether the virus can be produced by fermentation, but also an important indicator of the drug cost. Therefore, in this example, the single cell yield of the recombinant oncolytic adenovirus in medium-scale level was tested.

The engineered cell line for single cell yield test was HEK-293 cells from ATCC, which was commonly used in the art. The virus to be tested was inoculated into a certain number of engineered cells at different inoculation ratios (VP/cell), and 42 and 54 hours after the inoculation, the cells were broken and the progeny virus was collected for determining the VP number of the progeny virus, which was then divided by the number of cells at the time of inoculation to obtain the single cell yield.

The results are shown in Table 3. Both recombinant oncolytic adenoviruses rAd-IFN-1-SP-E1A(Δ24 bp)-E1B and rAd-IFN-3-SP-E1A(Δ24 bp)-E1B can achieve single cell yield required by industrial-scale production. The single cell yield of recombinant oncolytic adenovirus rAd-IFN-1-SP-E1A(Δ24 bp)-E1B reached the highest value after 42 hours of culture, but decreased after 54 hours of culture, indicating that the recombinant oncolysis adenovirus had a fast fermentation speed, which means that in industrial production, fermentation can be completed in a shorter time, so as to save costs. In comparison, the single cell yield of rAd-IFN-3-SP-E1A(Δ24 bp)-E1B reached the peak after 54 hours of culture, lower than the fermentation speed of rAd-IFN-1-SP-E1A(Δ24 bp)-E1B. Moreover, the single cell yield of rAd-IFN-1-SP-E1A(Δ24 bp)-E1B after 42 hours culture was higher than that of rAd-IFN-3-SP-E1A(Δ24 bp)-E1B after 56 hours culture, which means that the production efficiency of the former is also higher. Thus, in terms of single cell yield, the recombinant oncolytic adenovirus rAd-IFN-1-SP-E1A(Δ24 bp)-E1B has more advantages.

TABLE 3

Single cell yield of recombinant oncolytic adenovirus

| Harvest time (h) | Inoculation ratio (VP/cell) | rAd-IFN-1-SP-E1A(Δ24bp)-E1B (VP/cell) | rAd-IFN-3-SP-E1A(Δ24bp)-E1B (VP/cell) |
|---|---|---|---|
| 42 | 400:1 | 30200 | 20867 |
|  | 800:1 | 36900 | 19293 |
| 54 | 400:1 | 25000 | 25069 |
|  | 800:1 | 27100 | 25720 |

The invention claimed is:

1. An oncolytic virus comprising a nucleic acid encoding interferon, wherein the nucleic acid comprises a sequence selected from the group consisting of SEQ ID NO:2, 3 and 4.

2. The oncolytic virus according to claim 1, wherein the virus comprises adenovirus early region 1A (E1A) gene driven by a survivin promoter, the endogenous promoter of the E1A gene in viral genome is replaced by the survivin promoter; and/or the E1A gene is modified to reduce or completely inactivate the activity of E1A protein to bind to retinoblastoma (Rb) protein by deleting a sequence encoding amino acids 122-129 of the E1A protein encoded by nucleic acid residues 364-387 of SEQ ID NO: 1.

3. The oncolytic virus according to claim 1, wherein the nucleic acid sequence is operably linked to a cytomegalovirus (CMV) promoter.

4. The oncolytic virus according to claim 1, wherein the oncolytic virus is deposited at China Center for Type Culture Collection, under Accession number CCTCC NO: V201871, CCTCC NO: V201957 or CCTCC NO: V201958.

5. A pharmaceutical composition comprising a pharmaceutically effective amount of the oncolytic virus according to claim 1 and optionally a pharmaceutically acceptable carrier.

6. The pharmaceutical composition according to claim 5, wherein the pharmaceutical composition is formulated for intravenous, nebulized inhalation, perfusion, or intratumoral administration.

7. The pharmaceutical composition according to claim 5, comprising the oncolytic virus in an amount of about $10^8$ vp to $10^{12}$ vp.

8. A method for treating a proliferative disease, comprising administering the oncolytic virus according to claim 1 to a subject in need thereof, wherein the subject is a mammal, and the proliferative disease is a cancer.

9. A method for preventing or inhibiting metastasis of cancer cells, comprising administering the oncolytic virus according to claim 1 to a subject in need thereof, wherein the subject is a mammal.

10. A method for preventing cancer recurrence, comprising administering the oncolytic virus according to claim 1 to a subject in need thereof, wherein the subject is a mammal.

11. The method according to claim 8, wherein the oncolytic virus is administered to the subject in an amount of about $10^8$ vp to $10^{12}$ vp by intravenous, nebulized inhalation, perfusion, or intratumoral administration, with an administration number per treatment of 1-6, an administration interval of every 1, 2, 3, 4, 5, 6, 7 or more days, or 1, 2, 3, 4, 5, 6 or more times over the course of one day, and a treatment number of 1-12.

12. The method according to claim 8, wherein the cancer is selected from the group consisting of prostate cancer, breast cancer, colorectal cancer, lung cancer, liver cancer, melanoma, lymphoma, gastric cancer, esophageal cancer, ovarian cancer, head and neck squamous cell carcinoma, bladder cancer, glioma, cervical cancer, and kidney cancer.

13. The method according to claim 9, wherein the cancer is selected from the group consisting of prostate cancer, breast cancer, colorectal cancer, lung cancer, liver cancer, melanoma, lymphoma, gastric cancer, esophageal cancer, ovarian cancer, head and neck squamous cell carcinoma, bladder cancer, glioma, cervical cancer, and kidney cancer.

14. The method according to claim 10, wherein the cancer is selected from the group consisting of prostate cancer, breast cancer, colorectal cancer, lung cancer, liver cancer, melanoma, lymphoma, gastric cancer, esophageal cancer, ovarian cancer, head and neck squamous cell carcinoma, bladder cancer, glioma, cervical cancer, and kidney cancer.

15. The method according to claim 9, wherein the oncolytic virus is administered to the subject in an amount of about $10^8$ vp to $10^{12}$ vp by intravenous, nebulized inhalation, perfusion, or intratumoral administration, with an administration number per treatment of 1-6, an administration interval of every 1, 2, 3, 4, 5, 6, 7 or more days, or 1, 2, 3, 4, 5, 6 or more times over the course of one day, and a treatment number of 1-12.

16. The method according to claim 10, wherein the oncolytic virus is administered to the subject in an amount of about $10^8$ vp to $10^{12}$ vp by intravenous, nebulized inhalation, perfusion, or intratumoral administration, with an administration number per treatment of 1-6, an administration interval of every 1, 2, 3, 4, 5, 6, 7 or more days, or 1, 2, 3, 4, 5, 6 or more times over the course of one day, and a treatment number of 1-12.

* * * * *

SEQUENCE LISTING

<160> NUMBER OF SEQ ID NOS: 5

<210> SEQ ID NO 1
<211> LENGTH: 986
<212> TYPE: DNA
<213> ORGANISM: Adenovirus type 5

<400> SEQUENCE: 1

```
atgagacata ttatctgcca cggaggtgtt attaccgaag aaatggccgc cagtcttttg      60
gaccagctga tcgaagaggt actggctgat aatcttccac ctcctagcca ttttgaacca     120
cctacccttc acgaactgta tgatttagac gtgacggccc ccgaagatcc caacgaggag     180
gcggtttcgc agattttccc cgactctgta atgttggcgg tgcaggaagg gattgactta     240 ctcactttc cgccggcgcc cggttctccg gagccgcctc acctttcccg gcagcccgag     300
cagccggagc agagagcctt gggtccggtt tctatgccaa accttgtacc ggaggtgatc     360
gatcttacct gccacgaggc tggctttcca cccagtgacg acgaggatga agagggtgag     420
gagtttgtgt tagattatgt ggagcacccc gggcacggtt gcaggtcttg tcattatcac     480
cggaggaata cgggggaccc agatattatg tgttcgcttt gctatgag gacctgtggc      540 atgtttgtct acagtaagtg aaaattatgg gcagtgggtg atagagtggt gggtttggtg     600
tggtaatttt ttttttaatt tttacagttt tgtggtttaa agaattttgt attgtgattt     660
ttttaaaagg tcctgtgtct gaacctgagc ctgagcccga gccagaaccg gagcctgcaa     720
```

```
gacctacccg ccgtcctaaa atggcgcctg ctatcctgag acgcccgaca tcacctgtgt    780
ctagagaatg caatagtagt acggatagct gtgactccgg tccttctaac acacctcctg    840
agatacaccc ggtggtcccg ctgtgcccca ttaaaccagt tgccgtgaga gttggtgggc    900
gtcgccaggc tgtggaatgt atcgaggact tgcttaacga gcctgggcaa cctttggact    960
tgagctgtaa acgccccagg ccataa                                         986

<210> SEQ ID NO 2
<211> LENGTH: 573
<212> TYPE: DNA
<213> ORGANISM: Artificial Sequence
<220> FEATURE:
<223> OTHER INFORMATION: consensus interferon coding sequence IFN-1

<400> SEQUENCE: 2
atggccctgt ccttcagcct gctgatggcc gtgctggtgc tgagctacaa gtccatctgc     60
tccctgggca tgtgtgatct gcctcagaca cactccctgg caatagaag ggccctgatc    120 ctgctggccc agatgagaag gatcagcccc ttctcctgcc tgaaggatag acacgatttt    180
ggcttccctc aggaggagtt cgacggcaat cagtttcaga aggcccaggc catctccgtg    240
ctgcacgaga tgatccagca gacctttaac ctgttctcca caaggactc cagcgccgcc    300 tgggacgagt ccctgctgga aagttttac acagagctgt accagcagct gaacgatctg    360
gaggcctgcg tgatccagga ggtgggcgtg gaggagaccc ccctgatgaa tgtggattcc    420
atcctggccg tgaagaagta ctttcagaga atcaccctgt acctgaccga gaagaagtac    480
agcccttgtg cctgggaggt ggtgagagcc gagatcatga gatcctttc cctgagcaca    540 aacctgcagg agaggctgag aaggaaggag tga                                 573

<210> SEQ ID NO 3
<211> LENGTH: 573
<212> TYPE: DNA
<213> ORGANISM: Artificial Sequence
<220> FEATURE:
<223> OTHER INFORMATION: consensus interferon coding sequence IFN-2

<400> SEQUENCE: 3
atggccctgt ccttctccct gctgatggcc gtgctggtgc tgagctacaa gtccatctgc     60
tccctgggca tgtgcgacct gcctcagaca cactccctgg caataggag agccctgatc    120 ctgctggccc agatgaggag gatctccccct tttagctgcc tgaaggatag acacgatttc    180
ggcttccctc aggaggagtt cgatggcaat cagttccaga aggcccaggc catcagcgtg    240
ctgcacgaga tgatccagca gaccttcaat ctgtttagca ccaaggactc cagcgccgcc    300
tgggacgagt ccctgctgga aagttctac accgagctgt accagcagct gaacgacctg    360
gaggcctgcg tgatccagga ggtgggcgtg gaggagaccc ctctgatgaa tgtggatagc    420
atcctggccg tgaagaagta ctttcagaga atcacactgt acctgacaga gaagaagtac    480
agcccctgcg cctgggaggt ggtgagggct gagatcatga ggagcttttc cctgtccaca    540
aacctgcagg agaggctgag aaggaaggag tga                                 573

<210> SEQ ID NO 4
<211> LENGTH: 573
<212> TYPE: DNA
<213> ORGANISM: Artificial Sequence
<220> FEATURE:
<223> OTHER INFORMATION: consensus interferon coding sequence IFN-3
```

<400> SEQUENCE: 4

```
atggccctgt cctttctttt actgatggcc gtgctggtgc tcagctacaa atccatctgt    60
tctctgggca tgtgcgacct gccgcagacc cactccctgg gtaaccgtcg tgctctgatc   120
ctgctggctc agatgcgtcg tatctccccg ttctcctgcc tgaaagaccg tcacgacttc   180
ggtttcccgc aggaagaatt cgacggtaac cagttccaga agctcaggc tatctccgtt   240
ctgcacgaaa tgatccagca gaccttcaac ctgttctcca ccaaagactc tccgctgct   300
tgggacgaat ccctgctgga aaaattctac accgaactgt accagcagct gaacgacctg   360
gaagcttgcg ttatccagga agttggtgtt gaagaaaccc gctgatgaa cgttgactcc   420
atcctggctg ttaaaaaata cttccagcgt atcaccctgt acctgaccga aaaaaaatac   480
tccccgtgcg cttgggaagt tgttcgtgct gaaatcatgc gttccttctc cctgtccacc   540
aacctgcagg aacgtctgcg tcgtaaagaa taa                                573
```

<210> SEQ ID NO 5
<211> LENGTH: 2231
<212> TYPE: DNA
<213> ORGANISM: Artificial Sequence
<220> FEATURE:
<223> OTHER INFORMATION: Synthesized DNA for pShuttle-IFN-3-SP-
E1A(Δ24bp)-E1B construction

<400> SEQUENCE: 5

```
ataagaatgc ggccgcctcg actaattccc tggcattatg cccagtacat gaccttatgg    60
gactttccta cttggcagta catctacgta ttagtcatcg ctattaccat ggtgatgcgg   120
ttttggcagt acatcaatgg gcgtggatag cggtttgact cacggggatt ccaagtctc   180
cacccattg acgtcaatgg gagttgttt tggcaccaaa atcaacggga cttccaaaa    240
tgtcgtaaca actccgcccc attgacgcaa atgggcggta ggcgtgtacg gtgggaggtc   300
tatataagca gagctcgttt agtgaaccgt cagatcgcct ggagacgcca tccacgctgt   360
tttgacctcc atagaagaca ccgggaccga tccagcctgg ggatcttcga gtcgtcaagc   420
ttgaattcga tccccgggct gcaggaattc ccaatactat ggccctgtcc ttttctttac   480
tgatggccgt gctggtgctc agctacaaat ccatctgttc tctgggcatg tgcgacctgc   540
cgcagaccca ctccctgggt aaccgtcgtg ctctgatcct gctggctcag atgcgtcgta   600
tctccccgtt ctcctgcctg aaagaccgtc acgacttcgg tttcccgcag gaagaattcg   660
acggtaacca gttccagaaa gctcaggcta tctccgttct gcacgaaatg atccagcaga   720
ccttcaacct gttctccacc aaagactcct ccgctgcttg gacgaatcc ctgctggaaa   780
aattctacac cgaactgtac cagcagctga cgacctgga agcttgcgtt atccaggaag   840
ttggtgttga agaaacccg ctgatgaacg ttgactccat cctggctgtt aaaaaatact   900
tccagcgtat caccctgtac ctgaccgaaa aaaatactc ccgtgcgct gggaagttg    960
ttcgtgctga aatcatgcgt tccttctccc tgtccaccaa cctgcaggaa cgtctgcgtc  1020
gtaaagaata aggatccatc gagcaacttg tttattgcag cttataatgg ttacaaataa  1080
agcaatagca tcacaaattt cacaaataaa gcatttttt cactgcattc tagttgtggt  1140
ttgtccaaac tcatcaatgt atcttatcat gtctggatcg tgtcgagcgc gttctttgaa  1200
agcagtcgag ggggcgctag gtgtgggcag ggacgagctg gcggcgcgtc gctgggtgca  1260
ccgcgaccac gggcagagcc acgcggcggg aggactacaa ctcccggcac accccgcgcc  1320
gccccgcctc tactcccaga aggccgcggg gggtggaccg cctaagaggg cgtgcgctcc  1380
```

```
cgacatgccc cgcggcgcgc cattaaccgc cagatttgaa tcgccggacc cgttggcaga    1440
ggtggcggcg gcggcatacg tactgaaaat gagacatatt atctgccacg gaggtgttat    1500
taccgaagaa atggccgcca gtcttttgga ccagctgatc gaagaggtac tggctgataa    1560
tcttccacct cctagccatt ttgaaccacc tacccttcac gaactgtatg atttagacgt    1620
gacggccccc gaagatccca acgaggaggc ggtttcgcag attttcccg  actctgtaat    1680 gttggcggtg caggaaggga ttgacttact cacttttccg ccggcgcccg gttctccgga    1740
gccgcctcac ctttcccggc agcccgagca gccggagcag agagccttgg gtccggtttc    1800
tatgccaaac cttgtaccgg aggtgatcga tccacccagt gacgacgagg atgaagaggg    1860
tgaggagttt gtgttagatt atgtggagca ccccgggcac ggttgcaggt cttgtcatta    1920
tcaccggagg aatacggggg acccagatat tatgtgttcg ctttgctata tgaggacctg    1980
tggcatgttt gtctacagta agtgaaaatt atgggcagtg ggtgatagag tggtgggttt    2040
ggtgtggtaa ttttttttt  aattttaca  gttttgtggt ttaaagaatt ttgtattgtg    2100 attttttaa  aaggtcctgt gtctgaacct gagcctgagc ccgagccaga accggagcct    2160
gcaagaccta cccgccgtcc taaaatggcg cctgctatcc tgagacgccc gacatcacct    2220
gtgtctagag c                                                         2231
```